(12) United States Patent
Chang et al.

(10) Patent No.: US 9,541,480 B2
(45) Date of Patent: Jan. 10, 2017

(54) CAPTURE, PURIFICATION, AND RELEASE OF BIOLOGICAL SUBSTANCES USING A SURFACE COATING

(75) Inventors: Ying-Chih Chang, Taipei (TW); Han-Chung Wu, Taipei (TW); Po-Yuan Tseng, New Taipei (TW); Jen-Chia Wu, Magong (TW)

(73) Assignee: Academia Sinica, Taipei (TW)

( * ) Notice: Subject to any disclaimer, the term of this patent is extended or adjusted under 35 U.S.C. 154(b) by 308 days.

(21) Appl. No.: 14/128,354

(22) PCT Filed: Jun. 28, 2012

(86) PCT No.: PCT/US2012/044701
§ 371 (c)(1),
(2), (4) Date: May 20, 2014

(87) PCT Pub. No.: WO2013/003624
PCT Pub. Date: Jan. 3, 2013

(65) Prior Publication Data
US 2014/0255976 A1    Sep. 11, 2014

Related U.S. Application Data

(60) Provisional application No. 61/502,844, filed on Jun. 29, 2011, provisional application No. 61/606,220, filed on Mar. 2, 2012.

(51) Int. Cl.
| | | |
|---|---|---|
| *G01N 1/40* | (2006.01) | |
| *G01N 33/543* | (2006.01) | |
| *G01N 33/574* | (2006.01) | |
| *C07K 16/30* | (2006.01) | |
| *C07K 17/14* | (2006.01) | |

(52) U.S. Cl.
CPC ............ *G01N 1/405* (2013.01); *C07K 16/30* (2013.01); *C07K 17/14* (2013.01); *G01N 33/54393* (2013.01); *G01N 33/57492* (2013.01)

(58) Field of Classification Search
None
See application file for complete search history.

(56) References Cited

U.S. PATENT DOCUMENTS

| | | | |
|---|---|---|---|
| 5,554,686 A | 9/1996 | Frisch, Jr. et al. | |
| 5,646,001 A | 7/1997 | Terstappen et al. | |
| 5,707,799 A | 1/1998 | Hansmann et al. | |
| 5,837,115 A | 11/1998 | Austin et al. | |
| 5,842,787 A | 12/1998 | Kopf-Sill et al. | |
| 5,885,470 A | 3/1999 | Parce et al. | |
| 5,952,173 A | 9/1999 | Hansmann et al. | |
| 6,039,897 A | 3/2000 | Lochhead et al. | |
| 6,046,295 A | 4/2000 | Frisch, Jr. et al. | |
| 6,153,113 A | 11/2000 | Goodrich et al. | |
| 6,271,309 B1 | 8/2001 | Roberts et al. | |
| 6,280,622 B1 | 8/2001 | Goodrich et al. | |
| 6,322,683 B1 | 11/2001 | Wolk et al. | |
| 6,361,749 B1 | 3/2002 | Terstappen et al. | |
| 6,365,362 B1 | 4/2002 | Terstappen et al. | |
| 6,372,542 B1 | 4/2002 | Martin et al. | |
| 6,562,616 B1 | 5/2003 | Toner et al. | |
| 6,613,525 B2 | 9/2003 | Nelson et al. | |
| 6,620,627 B1 | 9/2003 | Liberti et al. | |
| 6,623,982 B1 | 9/2003 | Liberti et al. | |
| 6,632,652 B1 | 10/2003 | Austin et al. | |
| 6,645,731 B2 | 11/2003 | Terstappen et al. | |
| 6,685,841 B2 | 2/2004 | Lopez et al. | |
| 6,699,952 B2 | 3/2004 | Chaikof et al. | |
| 6,790,366 B2 | 9/2004 | Terstappen et al. | |
| 6,844,028 B2 | 1/2005 | Mao et al. | |

(Continued)

FOREIGN PATENT DOCUMENTS

| CN | 1646912 A | 7/2005 |
|---|---|---|
| CN | 102011193 A | 4/2011 |

(Continued)

OTHER PUBLICATIONS

Xu, Y. et al. 2009. Aptamer-based microfluidic device for enrichment, sorting, and detection of multiple cancer cells. Analytical Chemistry 81: 7436-7442. specif. pp. 7436, 7437, 7439, 7440.*
Phillips, J.A. et al. 2009. Enrichment of cancer cells using aptamers immobilized on a microfluidic channel. Analytical Chemistry 81: 1033-1039. specif. pp. 1034, 1035, 1036, 1037, 1038.*
Lin, J.J. et al. 2006. Adhesion of antibody-functionalized polymersomes. Langmuir 22: 3975-3979. specif. pp. 3975, 3979.*
Ananthanarayanan, et al. Neural stem cell adhesion and proliferation on phospholipid bilayers functionalized with RGD peptides. Biomaterials, Elsevier Science Publishers BV., Barking GB, vol. 31, No. 33, Nov. 1, 2010, pp. 8706-8715.
European search report and written opinion dated May 2, 2015 for EP Application No. 12805303.0.
Huang, et al. Type I Collagen-Functionalized Supported Lipid Bilayer as a Cell Culture Platform. Biomacromolecules, vol. 11, No. 5, May 10, 2010, pp. 1231-1240.

(Continued)

*Primary Examiner* — Renee Claytor
*Assistant Examiner* — Sharon M Papciak
(74) *Attorney, Agent, or Firm* — Wilson Sonsini Goodrich & Rosati

(57) ABSTRACT

This invention relates to a surface coating for capture circulating rare cells, comprising a nonfouling composition to prevent the binding of non-specific cells and adsorption of serum components; a bioactive composition for binding the biological substance, such as circulating tumor cells; with or without a linker composition that binds the nonfouling and bioactive compositions. The invention also provide a surface coating for capture and purification of a biological substance, comprising a releasable composition to release the non-specific cells and other serum components; a bioactive composition for binding the biological substance, such as circulating tumor cells; with or without a linker composition that binds the releasable and bioactive compositions. The present invention also discloses a novel microfluidic chip, with specific patterned microstructures to create a flow disturbance and increase the capture rate of the biological substance.

14 Claims, 33 Drawing Sheets

(56) References Cited

U.S. PATENT DOCUMENTS

| | | |
|---|---|---|
| 6,887,578 B2 | 5/2005 | Gleason et al. |
| 6,890,426 B2 | 5/2005 | Terstappen et al. |
| 6,955,738 B2 | 10/2005 | Derand et al. |
| 6,960,449 B2 | 11/2005 | Wang et al. |
| 7,005,493 B2 | 2/2006 | Huang et al. |
| 7,056,657 B2 | 6/2006 | Terstappen et al. |
| 7,067,194 B2 | 6/2006 | Mao et al. |
| 7,117,807 B2 | 10/2006 | Bohn, Jr. et al. |
| 7,150,812 B2 | 12/2006 | Huang et al. |
| 7,190,818 B2 | 3/2007 | Ellis et al. |
| 7,229,760 B2 | 6/2007 | Zohlnhöfer et al. |
| 7,276,170 B2 | 10/2007 | Oakey et al. |
| 7,282,350 B2 | 10/2007 | Rao et al. |
| 7,318,902 B2 | 1/2008 | Oakey et al. |
| 7,332,288 B2 | 2/2008 | Terstappen et al. |
| 7,368,163 B2 | 5/2008 | Huang et al. |
| 7,374,944 B2 | 5/2008 | Thompson et al. |
| 7,428,325 B2 | 9/2008 | Douglass et al. |
| 7,431,969 B2 | 10/2008 | Gleason et al. |
| 7,442,515 B2 | 10/2008 | Ratner et al. |
| 7,472,794 B2 | 1/2009 | Oakey et al. |
| 7,485,343 B1 | 2/2009 | Branson et al. |
| 7,501,157 B2 | 3/2009 | Mao et al. |
| 7,531,120 B2 | 5/2009 | Van Rijn et al. |
| 7,579,077 B2 | 8/2009 | Dubrow et al. |
| 7,588,550 B2 | 9/2009 | Leonard et al. |
| 7,629,029 B2 | 12/2009 | Mao et al. |
| 7,687,241 B2 | 3/2010 | Chen |
| 7,695,775 B2 | 4/2010 | Kobrin et al. |
| 7,713,689 B2 | 5/2010 | Chilkoti |
| 7,723,112 B2 | 5/2010 | Clarke et al. |
| 7,727,399 B2 | 6/2010 | Leonard et al. |
| 7,735,652 B2 | 6/2010 | Inglis et al. |
| 7,736,891 B2 | 6/2010 | Nelson et al. |
| 7,777,010 B2 | 8/2010 | Logtenberg |
| 7,783,098 B2 | 8/2010 | Douglass et al. |
| 7,785,810 B2 | 8/2010 | Chen |
| RE41,762 E | 9/2010 | Lopez et al. |
| 7,815,922 B2 | 10/2010 | Chaney et al. |
| 7,846,393 B2 | 12/2010 | Tai et al. |
| 7,846,445 B2 | 12/2010 | Schellenberger et al. |
| 7,846,743 B2 | 12/2010 | Tai et al. |
| 7,850,633 B2 | 12/2010 | Leonard et al. |
| 7,855,068 B2 | 12/2010 | Cao |
| 7,855,279 B2 | 12/2010 | Schellenberger et al. |
| 7,863,012 B2 | 1/2011 | Tao et al. |
| 7,879,444 B2 | 2/2011 | Jiang et al. |
| RE42,249 E | 3/2011 | Lopez et al. |
| 7,901,950 B2 | 3/2011 | Connelly et al. |
| RE42,315 E | 5/2011 | Lopez et al. |
| 7,955,704 B2 | 6/2011 | Lowery et al. |
| 7,960,166 B2 | 6/2011 | Vacanti et al. |
| 7,973,136 B2 | 7/2011 | Lazar et al. |
| 7,981,688 B2 | 7/2011 | Stayton et al. |
| 7,985,475 B2 | 7/2011 | Dubrow |
| 7,988,840 B2 | 8/2011 | Huang et al. |
| 7,993,821 B2 | 8/2011 | Chiu et al. |
| 8,008,032 B2 | 8/2011 | Forsyth et al. |
| 8,012,480 B2 | 9/2011 | Lorence |
| 8,021,318 B2 | 9/2011 | Leonard et al. |
| 8,021,614 B2 | 9/2011 | Huang et al. |
| 8,025,854 B2 | 9/2011 | Ohman et al. |
| 8,057,418 B2 | 11/2011 | Korbling et al. |
| 8,063,187 B2 | 11/2011 | Chu et al. |
| 8,069,782 B2 | 12/2011 | Fragala et al. |
| 8,083,706 B2 | 12/2011 | Leonard et al. |
| 8,092,684 B2 | 1/2012 | Leonard et al. |
| 8,093,365 B2 | 1/2012 | Wisniewski et al. |
| 8,097,153 B2 | 1/2012 | Leonard et al. |
| 8,097,162 B2 | 1/2012 | Leonard et al. |
| 8,101,720 B2 | 1/2012 | Lazar et al. |
| 8,158,410 B2 | 4/2012 | Tang et al. |
| 8,158,728 B2 | 4/2012 | Desimone et al. |
| 8,178,602 B2 | 5/2012 | Mao et al. |
| 8,186,913 B2 | 5/2012 | Toner et al. |
| 8,282,799 B2 | 10/2012 | Huang et al. |
| 8,288,116 B2 | 10/2012 | Chen |
| 8,288,170 B2 | 10/2012 | Tai et al. |
| 8,304,230 B2 | 11/2012 | Toner et al. |
| 8,308,699 B2 | 11/2012 | Zhang et al. |
| 8,333,934 B2 | 12/2012 | Cao et al. |
| 8,343,440 B2 | 1/2013 | Yoshioka |
| 8,357,528 B2 | 1/2013 | Vacanti et al. |
| 8,367,314 B2 | 2/2013 | Chilkoti |
| 8,372,579 B2 | 2/2013 | Toner et al. |
| 8,414,806 B2 | 4/2013 | Sun et al. |
| 8,445,225 B2 | 5/2013 | Kuhn et al. |
| 8,481,336 B2 | 7/2013 | Earhart et al. |
| 8,491,516 B2 | 7/2013 | Leonard et al. |
| 8,507,283 B2 | 8/2013 | Stayton et al. |
| 8,545,983 B2 | 10/2013 | Jiang et al. |
| 8,557,528 B2 | 10/2013 | Hauch et al. |
| 8,557,577 B2 | 10/2013 | Hauch et al. |
| 8,574,660 B2 | 11/2013 | Weaver et al. |
| 8,579,117 B2 | 11/2013 | Sturm et al. |
| 8,632,838 B2 | 1/2014 | Roth et al. |
| 8,663,625 B2 | 3/2014 | Stroock et al. |
| 8,669,044 B2 | 3/2014 | Chiu et al. |
| 8,796,184 B2 | 8/2014 | Chilkoti et al. |
| 8,821,812 B2 | 9/2014 | Ohman et al. |
| 8,822,231 B2 | 9/2014 | Melin et al. |
| 8,835,144 B2 | 9/2014 | Jiang et al. |
| 8,895,298 B2 | 11/2014 | Toner et al. |
| 8,911,957 B2 | 12/2014 | Irimia et al. |
| 8,921,102 B2 | 12/2014 | Fuchs et al. |
| 8,980,568 B2 | 3/2015 | Lin et al. |
| 8,986,966 B2 | 3/2015 | Toner et al. |
| 8,986,988 B2 | 3/2015 | Karnik et al. |
| 9,016,221 B2 | 4/2015 | Brennan et al. |
| 9,056,318 B2 | 6/2015 | Bergman et al. |
| 9,140,697 B2 | 9/2015 | Tseng et al. |
| 9,174,222 B2 | 11/2015 | Huang et al. |
| 2001/0031309 A1 | 10/2001 | Lee et al. |
| 2001/0036556 A1 | 11/2001 | Jen |
| 2002/0009759 A1 | 1/2002 | Terstappen et al. |
| 2002/0055093 A1 | 5/2002 | Abbott et al. |
| 2002/0098535 A1 | 7/2002 | Wang et al. |
| 2002/0119482 A1 | 8/2002 | Nelson et al. |
| 2002/0125192 A1 | 9/2002 | Lopez et al. |
| 2002/0141913 A1 | 10/2002 | Terstappen et al. |
| 2002/0160139 A1 | 10/2002 | Huang et al. |
| 2002/0182633 A1 | 12/2002 | Chen et al. |
| 2003/0022216 A1 | 1/2003 | Mao et al. |
| 2003/0087338 A1 | 5/2003 | Messersmith et al. |
| 2003/0096226 A1 | 5/2003 | Logtenberg |
| 2003/0129676 A1 | 7/2003 | Terstappen et al. |
| 2003/0138645 A1 | 7/2003 | Gleason et al. |
| 2003/0157054 A1* | 8/2003 | Gillies ............... C07K 16/30 424/85.1 |
| 2003/0159999 A1 | 8/2003 | Oakey et al. |
| 2003/0206901 A1 | 11/2003 | Chen |
| 2003/0213551 A1 | 11/2003 | Derand et al. |
| 2003/0216534 A1 | 11/2003 | Chaikof et al. |
| 2004/0004043 A1 | 1/2004 | Terstappen et al. |
| 2004/0009471 A1 | 1/2004 | Cao |
| 2004/0028875 A1 | 2/2004 | Van Rijn et al. |
| 2004/0038339 A1 | 2/2004 | Kufer et al. |
| 2004/0053334 A1 | 3/2004 | Ratner et al. |
| 2004/0072269 A1 | 4/2004 | Rao et al. |
| 2004/0109853 A1 | 6/2004 | McDaniel |
| 2004/0115721 A1 | 6/2004 | Mao et al. |
| 2004/0118757 A1 | 6/2004 | Terstappen et al. |
| 2004/0175407 A1 | 9/2004 | McDaniel |
| 2004/0225249 A1 | 11/2004 | Leonard et al. |
| 2004/0254419 A1 | 12/2004 | Wang et al. |
| 2005/0025797 A1 | 2/2005 | Wang et al. |
| 2005/0042766 A1 | 2/2005 | Ohman et al. |
| 2005/0079132 A1 | 4/2005 | Wang et al. |
| 2005/0100675 A1 | 5/2005 | Mao et al. |
| 2005/0107870 A1 | 5/2005 | Wang et al. |
| 2005/0147758 A1 | 7/2005 | Mao et al. |
| 2005/0153342 A1 | 7/2005 | Chen |
| 2005/0175501 A1 | 8/2005 | Thompson et al. |
| 2005/0178286 A1 | 8/2005 | Bohn, Jr. et al. |

(56) References Cited

U.S. PATENT DOCUMENTS

| | | |
|---|---|---|
| 2005/0181195 A1 | 8/2005 | Dubrow |
| 2005/0181463 A1 | 8/2005 | Rao et al. |
| 2005/0186685 A1 | 8/2005 | Kange et al. |
| 2005/0215764 A1 | 9/2005 | Tuszynski et al. |
| 2005/0230272 A1 | 10/2005 | Lee et al. |
| 2005/0255327 A1 | 11/2005 | Chaney et al. |
| 2005/0265980 A1 | 12/2005 | Chen et al. |
| 2005/0267440 A1 | 12/2005 | Herman et al. |
| 2005/0288398 A1 | 12/2005 | Messersmith et al. |
| 2006/0002825 A1 | 1/2006 | Derand et al. |
| 2006/0009550 A1 | 1/2006 | Messersmith et al. |
| 2006/0014013 A1 | 1/2006 | Saavedra et al. |
| 2006/0057180 A1 | 3/2006 | Chilkoti et al. |
| 2006/0076295 A1 | 4/2006 | Leonard et al. |
| 2006/0079740 A1 | 4/2006 | Silver et al. |
| 2006/0088666 A1 | 4/2006 | Kobrin et al. |
| 2006/0093836 A1 | 5/2006 | Huang et al. |
| 2006/0134599 A1 | 6/2006 | Toner et al. |
| 2006/0159916 A1 | 7/2006 | Dubrow et al. |
| 2006/0160066 A1 | 7/2006 | Bhatia et al. |
| 2006/0166183 A1 | 7/2006 | Short et al. |
| 2006/0169642 A1 | 8/2006 | Oakey et al. |
| 2006/0173394 A1 | 8/2006 | Stroock et al. |
| 2006/0194192 A1 | 8/2006 | Rao et al. |
| 2006/0237390 A1 | 10/2006 | King et al. |
| 2006/0251795 A1 | 11/2006 | Kobrin et al. |
| 2006/0252046 A1 | 11/2006 | Short et al. |
| 2006/0252054 A1 | 11/2006 | Lin et al. |
| 2006/0254972 A1 | 11/2006 | Tai et al. |
| 2006/0285996 A1 | 12/2006 | Ohman et al. |
| 2007/0003549 A1 | 1/2007 | Ignatovich et al. |
| 2007/0010702 A1 | 1/2007 | Wang et al. |
| 2007/0025883 A1 | 2/2007 | Tai et al. |
| 2007/0026381 A1 | 2/2007 | Huang et al. |
| 2007/0026416 A1 | 2/2007 | Fuchs |
| 2007/0026469 A1 | 2/2007 | Fuchs et al. |
| 2007/0032620 A1 | 2/2007 | Gleason et al. |
| 2007/0037173 A1 | 2/2007 | Allard et al. |
| 2007/0048859 A1 | 3/2007 | Sears |
| 2007/0059716 A1 | 3/2007 | Balis et al. |
| 2007/0071762 A1 | 3/2007 | Ts'o et al. |
| 2007/0072220 A1 | 3/2007 | Chilkoti |
| 2007/0077276 A1 | 4/2007 | Haynie |
| 2007/0122406 A1 | 5/2007 | Chamberlain et al. |
| 2007/0131622 A1 | 6/2007 | Oakey et al. |
| 2007/0154960 A1 | 7/2007 | Connelly et al. |
| 2007/0172903 A1 | 7/2007 | Toner et al. |
| 2007/0178133 A1 | 8/2007 | Rolland |
| 2007/0187250 A1 | 8/2007 | Huang et al. |
| 2007/0202536 A1 | 8/2007 | Yamanishi et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2007/0266777 A1 | 11/2007 | Bergman et al. |
| 2007/0281353 A1 | 12/2007 | Vacanti et al. |
| 2008/0009780 A1 | 1/2008 | Leonard et al. |
| 2008/0023399 A1 | 1/2008 | Inglis et al. |
| 2008/0026486 A1 | 1/2008 | Cooper et al. |
| 2008/0090239 A1 | 4/2008 | Shoemaker et al. |
| 2008/0113350 A1 | 5/2008 | Terstappen |
| 2008/0114096 A1 | 5/2008 | Qu et al. |
| 2008/0131425 A1 | 6/2008 | Garcia et al. |
| 2008/0147178 A1 | 6/2008 | Pacetti et al. |
| 2008/0149566 A1 | 6/2008 | Messersmith et al. |
| 2008/0176271 A1 | 7/2008 | Silver et al. |
| 2008/0181861 A1 | 7/2008 | Jiang et al. |
| 2008/0188638 A1 | 8/2008 | Breitenkamp et al. |
| 2008/0207913 A1 | 8/2008 | Breitenkamp et al. |
| 2008/0213853 A1 | 9/2008 | Garcia et al. |
| 2008/0220531 A1 | 9/2008 | Stayton et al. |
| 2008/0241892 A1 | 10/2008 | Roitman et al. |
| 2008/0248499 A1 | 10/2008 | Chiu et al. |
| 2008/0255305 A1 | 10/2008 | Brook et al. |
| 2008/0274335 A1 | 11/2008 | Bowman et al. |
| 2008/0311182 A1 | 12/2008 | Ferrari et al. |
| 2008/0312356 A1 | 12/2008 | Kobrin et al. |
| 2009/0020431 A1 | 1/2009 | Voccia et al. |
| 2009/0029043 A1 | 1/2009 | Rong et al. |
| 2009/0060791 A1 | 3/2009 | Hagiwara et al. |
| 2009/0068760 A1 | 3/2009 | Nelson et al. |
| 2009/0093610 A1 | 4/2009 | Textor et al. |
| 2009/0098017 A1 | 4/2009 | Celik-butler et al. |
| 2009/0105463 A1 | 4/2009 | Berry et al. |
| 2009/0114344 A1 | 5/2009 | Barinov et al. |
| 2009/0117574 A1 | 5/2009 | Labgold et al. |
| 2009/0136982 A1 | 5/2009 | Tang et al. |
| 2009/0139931 A1 | 6/2009 | Leonard et al. |
| 2009/0142772 A1 | 6/2009 | Lau et al. |
| 2009/0156460 A1 | 6/2009 | Jiang et al. |
| 2009/0181441 A1 | 7/2009 | Jin et al. |
| 2009/0203536 A1 | 8/2009 | Vermette et al. |
| 2009/0215088 A1 | 8/2009 | Forsyth et al. |
| 2009/0226499 A1 | 9/2009 | Wisniewski et al. |
| 2009/0247424 A1 | 10/2009 | Chilkoti et al. |
| 2009/0259015 A1 | 10/2009 | Jiang et al. |
| 2009/0259302 A1 | 10/2009 | Trollsas et al. |
| 2009/0263457 A1 | 10/2009 | Trollsas et al. |
| 2009/0264317 A1 | 10/2009 | Ofir et al. |
| 2009/0269323 A1 | 10/2009 | Luk et al. |
| 2009/0281250 A1 | 11/2009 | Desimone et al. |
| 2009/0285873 A1 | 11/2009 | Lim et al. |
| 2009/0292234 A1 | 11/2009 | Leonard et al. |
| 2009/0298067 A1 | 12/2009 | Irimia et al. |
| 2009/0311734 A1 | 12/2009 | Greve et al. |
| 2009/0317836 A1 | 12/2009 | Kuhn et al. |
| 2010/0004578 A1 | 1/2010 | Leonard et al. |
| 2010/0028526 A1 | 2/2010 | Martin et al. |
| 2010/0055733 A1 | 3/2010 | Lutolf et al. |
| 2010/0059414 A1 | 3/2010 | Sturm et al. |
| 2010/0061892 A1 | 3/2010 | Flaim et al. |
| 2010/0062156 A1 | 3/2010 | Kurth et al. |
| 2010/0063570 A1 | 3/2010 | Pacetti et al. |
| 2010/0081735 A1 | 4/2010 | Mao et al. |
| 2010/0092393 A1 | 4/2010 | Haghgooie et al. |
| 2010/0092491 A1 | 4/2010 | Anastasi et al. |
| 2010/0096327 A1 | 4/2010 | Gin et al. |
| 2010/0099160 A1 | 4/2010 | Jiang et al. |
| 2010/0099579 A1 | 4/2010 | Chilkoti |
| 2010/0112026 A1* | 5/2010 | Karp ............ A61L 27/34 424/422 |
| 2010/0118642 A1 | 5/2010 | Ho et al. |
| 2010/0137984 A1 | 6/2010 | Lowery et al. |
| 2010/0140160 A1 | 6/2010 | Dubrow et al. |
| 2010/0143438 A1 | 6/2010 | Todd et al. |
| 2010/0143741 A1 | 6/2010 | Bell et al. |
| 2010/0145286 A1 | 6/2010 | Zhang et al. |
| 2010/0151491 A1 | 6/2010 | Himmelhaus et al. |
| 2010/0152708 A1 | 6/2010 | Li et al. |
| 2010/0159462 A1 | 6/2010 | Takayama et al. |
| 2010/0160645 A1 | 6/2010 | Breitenkamp et al. |
| 2010/0169990 A1 | 7/2010 | Clarke et al. |
| 2010/0173402 A1 | 7/2010 | Chen |
| 2010/0198131 A1 | 8/2010 | Leonard et al. |
| 2010/0209612 A1 | 8/2010 | Rong et al. |
| 2010/0210745 A1 | 8/2010 | Mcdaniel et al. |
| 2010/0226943 A1 | 9/2010 | Brennan et al. |
| 2010/0233146 A1 | 9/2010 | McDaniel |
| 2010/0233693 A1 | 9/2010 | Kopf-Sill et al. |
| 2010/0233694 A1 | 9/2010 | Kopf-Sill |
| 2010/0233812 A1 | 9/2010 | Sun et al. |
| 2010/0247492 A1 | 9/2010 | Kuhn et al. |
| 2010/0247760 A1 | 9/2010 | Houben et al. |
| 2010/0248334 A1 | 9/2010 | McDaniel |
| 2010/0248358 A1 | 9/2010 | Yoshioka |
| 2010/0273991 A1 | 10/2010 | Luk et al. |
| 2010/0278892 A1 | 11/2010 | Krauland et al. |
| 2010/0279321 A1 | 11/2010 | Chiu et al. |
| 2010/0280252 A1 | 11/2010 | Breitenkamp et al. |
| 2010/0285581 A1 | 11/2010 | Hauch et al. |
| 2010/0285972 A1 | 11/2010 | Dubrow et al. |
| 2010/0294146 A1 | 11/2010 | Fragala et al. |
| 2010/0304485 A1 | 12/2010 | Karnik et al. |
| 2010/0311599 A1 | 12/2010 | Wheeler et al. |
| 2010/0316842 A1 | 12/2010 | Tuteja et al. |

(56) References Cited

U.S. PATENT DOCUMENTS

| | | |
|---|---|---|
| 2010/0323918 A1 | 12/2010 | Huang et al. |
| 2010/0330025 A1 | 12/2010 | Messersmith et al. |
| 2010/0331965 A1 | 12/2010 | Dugas |
| 2011/0005997 A1 | 1/2011 | Kurth et al. |
| 2011/0008404 A1 | 1/2011 | Lyon et al. |
| 2011/0027803 A1 | 2/2011 | Moussavi et al. |
| 2011/0048947 A1 | 3/2011 | Petronis et al. |
| 2011/0054347 A1 | 3/2011 | Goss et al. |
| 2011/0056884 A1 | 3/2011 | Leonard et al. |
| 2011/0059468 A1 | 3/2011 | Earhart et al. |
| 2011/0062083 A1 | 3/2011 | Leonard et al. |
| 2011/0066097 A1 | 3/2011 | Leonard et al. |
| 2011/0097277 A1 | 4/2011 | Jiang et al. |
| 2011/0105712 A1 | 5/2011 | Jiang et al. |
| 2011/0105982 A1 | 5/2011 | Leonard et al. |
| 2011/0117674 A1 | 5/2011 | Melin et al. |
| 2011/0143119 A1 | 6/2011 | Bell et al. |
| 2011/0165161 A1 | 7/2011 | Lin et al. |
| 2011/0165415 A1 | 7/2011 | Ma et al. |
| 2011/0171663 A1 | 7/2011 | Smith et al. |
| 2011/0192233 A1 | 8/2011 | Aizenberg et al. |
| 2011/0195104 A1 | 8/2011 | Jiang et al. |
| 2011/0212085 A1 | 9/2011 | Joseloff et al. |
| 2011/0212297 A1 | 9/2011 | Dhinojwala et al. |
| 2011/0212440 A1 | 9/2011 | Viovy et al. |
| 2011/0217449 A1 | 9/2011 | Lowery et al. |
| 2011/0224383 A1 | 9/2011 | Sill et al. |
| 2011/0236904 A1 | 9/2011 | Hauch et al. |
| 2011/0240064 A1 | 10/2011 | Wales et al. |
| 2011/0240595 A1 | 10/2011 | Dubrow |
| 2011/0250626 A1 | 10/2011 | Williams et al. |
| 2011/0250679 A1 | 10/2011 | Chang |
| 2011/0256619 A1 | 10/2011 | Vacanti et al. |
| 2011/0266492 A1 | 11/2011 | Stayton et al. |
| 2011/0275530 A1 | 11/2011 | Walfish et al. |
| 2011/0282005 A1 | 11/2011 | Jiang et al. |
| 2011/0294186 A1 | 12/2011 | Fuchs et al. |
| 2011/0300551 A1 | 12/2011 | Rao et al. |
| 2011/0300603 A1 | 12/2011 | Forsyth et al. |
| 2011/0301442 A1 | 12/2011 | Lucke et al. |
| 2011/0305660 A1 | 12/2011 | Stayton et al. |
| 2011/0305872 A1 | 12/2011 | Li et al. |
| 2011/0305881 A1 | 12/2011 | Schultz et al. |
| 2011/0305895 A1 | 12/2011 | Roth et al. |
| 2011/0305898 A1 | 12/2011 | Zhang et al. |
| 2011/0305909 A1 | 12/2011 | Weaver et al. |
| 2012/0003711 A1 | 1/2012 | Tseng et al. |
| 2012/0006728 A1 | 1/2012 | Huang et al. |
| 2012/0015146 A1 | 1/2012 | Advincula et al. |
| 2012/0015835 A1 | 1/2012 | Fuchs et al. |
| 2012/0021200 A1 | 1/2012 | Koberstein et al. |
| 2012/0028342 A1 | 2/2012 | Ismagilov et al. |
| 2012/0037544 A1 | 2/2012 | Lane et al. |
| 2012/0045828 A1 | 2/2012 | Davis et al. |
| 2012/0052415 A1 | 3/2012 | Fragala et al. |
| 2012/0058302 A1 | 3/2012 | Eggenspieler et al. |
| 2012/0058500 A1 | 3/2012 | Mitchell et al. |
| 2012/0061304 A1 | 3/2012 | Leonard et al. |
| 2012/0064150 A1 | 3/2012 | Wisniewski et al. |
| 2012/0077246 A1 | 3/2012 | Hong et al. |
| 2012/0114742 A1 | 5/2012 | Martinez et al. |
| 2012/0178094 A1 | 7/2012 | Kuhn |
| 2012/0196273 A1 | 8/2012 | Huang et al. |
| 2012/0252022 A1 | 10/2012 | Walfish et al. |
| 2012/0270209 A1 | 10/2012 | Shah et al. |
| 2012/0301900 A1 | 11/2012 | Kang et al. |
| 2013/0143197 A1 | 6/2013 | Heyneker et al. |

FOREIGN PATENT DOCUMENTS

| | | |
|---|---|---|
| EP | 0783694 B1 | 11/2003 |
| EP | 2359689 A1 | 8/2011 |
| EP | 1569510 B1 | 11/2011 |
| EP | 2359689 B1 | 8/2015 |
| GB | 2427468 B | 3/2011 |
| GB | 2472927 B | 5/2011 |
| WO | WO 98/23948 A1 | 6/1998 |
| WO | WO-9920649 A1 | 4/1999 |
| WO | WO-2007048459 A1 | 5/2007 |
| WO | WO 2009/088933 A1 | 7/2009 |
| WO | WO 2009/140326 A2 | 11/2009 |
| WO | WO 2010/123608 A2 | 10/2010 |
| WO | WO 2010/124227 A2 | 10/2010 |
| WO | WO 2010/132795 A2 | 11/2010 |
| WO | WO 2012/016136 A2 | 2/2012 |
| WO | WO 2012/094642 A2 | 7/2012 |
| WO | WO 2012/103025 A2 | 8/2012 |
| WO | WO 2012/116073 A2 | 8/2012 |
| WO | WO 2013/006828 A1 | 1/2013 |
| WO | WO-2013003624 A2 | 1/2013 |
| WO | WO 2013/036620 A1 | 3/2013 |

OTHER PUBLICATIONS

Ishihara, et al. Photoinduced graft polymerization of 2-methacryloyloxyethyl phosphorylcholine on polyethylene membrane surface for obtaining blood cell adhesion resistance. Colloids and Surfaces B: Biointerfaces, vol. 18, No. 3-4, Oct. 1, 2000, pp. 325-355.

Alix-Panabieres, et al. Challenges in circulating tumour cell research. Nat Rev Cancer. Sep. 2014;14(9):623-31. doi: 10.1038/nrc3820. Epub Jul. 31, 2014.

Antolovic, et al. Heterogeneous detection of circulating tumor cells in patients with colorectal cancer by immunomagnetic enrichment using different EpCAM-specific antibodies. BMC Biotechnol. Apr. 28, 2010;10:35. doi: 10.1186/1472-6750-10-35.

Baeuerle, et al. EpCAM (CD326) finding its role in cancer. Br J Cancer. Feb. 12, 2007;96(3):417-23. Epub Jan. 9, 2007.

Balzar, et al. Epidermal growth factor-like repeats mediate lateral and reciprocal interactions of Ep-CAM molecules in homophilic adhesions. Mol Cell Biol. Apr. 2001;21(7):2570-80.

Chaudry, et al. EpCAM an immunotherapeutic target for gastrointestinal malignancy: current experience and future challenges. Br J Cancer. Apr. 10, 2007;96(7):1013-9. Epub Feb. 27, 2007.

Cornell, et al. A biosensor that uses ion-channel switches. Letters to Nauture. Jun. 5, 1997. vol. 387. p. 580-583.

Gervais, Luc. Capillary Microfluidic Chips for Point-of-Care Testing: from Research Tools to Decentralized Medical Diagnostics. InfoScience. 2011. Thesis 5047. Available at http://infoscience.epfl.ch/record/165376/files/EPFL_TH5047.pdf.

Holmen, et al. Heterogeneity of human nasal vascular and sinusoidal endothelial cells from the inferior turbinate. Am J Respir Cell Mol Biol. Jan. 2005;32(1):18-27. Epub Oct. 21, 2004.

International search report and written opinion dated May 30, 2013 for PCT Application No. PCT/US2013/028667 with publication.

Karabacak, et al. Microfluidic, marker-free isolation of circulating tumor cells from blood samples. Nat Protoc. Mar. 2014;9(3):694-710. doi: 10.1038/nprot.2014.044. Epub Feb. 27, 2014.

NCBI Direct Submission. NM_002354.2. *Homo sapiens* epithelial cell adhesion molecule (EPCAM), mRNA. Feb. 5, 2012. [Retrieved from the Internet: <http://www.ncbi.nlm.nih.gov/nuccore/218505669?sat=15&satkey=5763417>.

Patriarca, et al. Epithelial cell adhesion molecule expression (CD326) in cancer: a short review. Cancer Treat Rev. Feb. 2012;38(1):68-75. doi: 10.1016/j.ctrv.2011.04.002. Epub May 14, 2011.

Ruf, et al. Characterisation of the new EpCAM-specific antibody HO-3: implications for trifunctional antibody immunotherapy of cancer. Br J Cancer. Aug. 6, 2007;97(3):315-21. Epub Jul. 10, 2007.

Chen, et al. Generation and characterization of monoclonal antibodies against dengue virus type 1 for epitope mapping and serological detection by epitope-based peptide antigens. Clin Vaccine Immunol. Apr. 2007;14(4):404-11. Epub Feb. 7, 2007.

International search report and written opinion dated Dec. 10, 2012 for PCT/US2012/044701.

Johnson, et al. Structure of an adsorbed dimyristoylphosphatidylcholine bilayer measured with specular reflection of neutrons. Biophys J. Feb. 1991;59(2):289-94.

(56) References Cited

OTHER PUBLICATIONS

Kahn, et al. Enumeration of circulating tumor cells in the blood of breast cancer patients after filtration enrichment: correlation with disease stage. Breast Cancer Res Treat. Aug. 2004;86(3):237-47.

Kaladhar, et al. Cell mimetic lateral stabilization of outer cell mimetic bilayer on polymer surfaces by peptide bonding and their blood compatibility. J Biomed Mater Res A. Oct. 2006;79(1):23-35.

Kaladhar, et al. Supported cell mimetic monolayers and their interaction with blood. Langmuir. Dec 7, 2004;20(25):11115-22.

Nagrath, et al. Isolation of rare circulating tumour cells in cancer patients by microchip technology. Nature. Dec. 20, 2007;450(7173):1235-9.

Pantel, et al. Detection, clinical relevance and specific biological properties of disseminating tumour cells. Nat Rev Cancer. May 2008;8(5):329-40. doi: 10.1038/nrc2375.

Yurke, et al. A DNA-fuelled molecular machine made of DNA. Nature. Aug. 10, 2000;406(6796):605-8.

European search report dated Jan. 29, 2016 for EP 15182577.5.
Office action dated Jan. 21, 2015 for U.S. Appl. No. 14/065,265.
Office action dated Mar. 9, 2016 for U.S. Appl. No. 14/065,265.
Office action dated May 29, 2015 for U.S. Appl. No. 14/065,265.
Office action dated Mar. 23, 2016 for U.S. Appl. No. 14/128,345.

Phillips, J.A. et al. 2009. Enrichment of cancer cells using aptamers immobilized on a microfluidic channel. Analytical Chemistry 81 : 1 033-1 039. specif. pp. 1 034, 1 035, 1 036, 1 037, 1 038.

Xu, Y. et al. 2009. Aptamer-based microfluidic device for enrichment, sorting, and detection of multiple cancer cells. AnalyticalChemistry 81: 7436-7442. specif. pp. 7436, 7437, 7439, 7440.

Lawrence, et al. Leukocytes roll on a selectin at physiologic flow rates: distinction from and prerequisite for adhesion through integrins.Cell. May 31, 1991;65(5):859-73.

Notice of allowance dated Jul. 7, 2016 for U.S. Appl. No. 14/065,265.

* cited by examiner

Fig. 15A
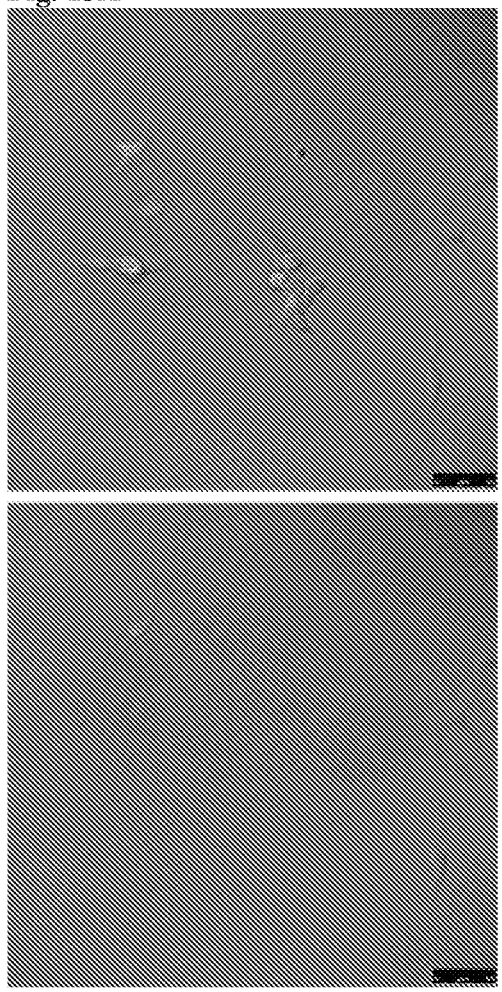
Fig. 15 B
Fig. 15C
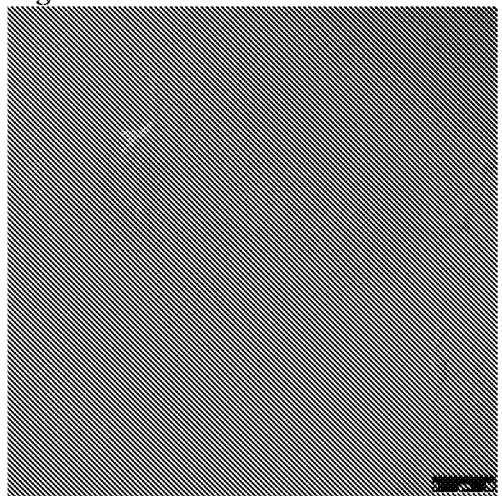

T=10.50 min

T=10.504 min

T=10.55 min

CAPTURE, PURIFICATION, AND RELEASE OF BIOLOGICAL SUBSTANCES USING A SURFACE COATING

CROSS-REFERENCES TO RELATED APPLICATIONS

This application claims the benefit of U.S. Provisional Application Ser. No. 61/502,844, filed Jun. 29, 2011, and U.S. Provisional Application Ser. No. 61/606,220, filed Mar. 2, 2012, each of which are hereby incorporated by reference in their entirety for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

The instant application contains a Sequence Listing which has been submitted in ASCII format via EFS-Web and is hereby incorporated by reference in its entirety. Said ASCII copy, created on May 7, 2014, is named "45249-701.831-Seqlist.txt" and is 4,047 bytes in size.

BACKGROUND OF THE INVENTION

The shedding of cells into the circulation is an intrinsic property of the malignant tumor, and this feature provides important information with regard to the diagnosis, staging, treatment response and survival of cancer patients. For example, Pantel et al found the number of circulating tumor cells (CTCs) in the blood is correlated with the aggressiveness of the cancer as well as the efficacy of the therapy. (Pantel, K. et. al., "Detection, clinical relevance and specific biological properties of disseminating tumor cells", *Nat Rev Cancer,* 2008, 8(5):329-40).

However, CTCs, as few as one per 109 blood cells in patients with metastatic cancer, are rare cells. This makes the detection and isolation of CTCs technically challenging (see Kahnet al. *Breast Cancer Res Treat* 2004, 86:237-47). An enrichment process is therefore necessary to effectively detect and isolate CTCs.

An example of such enrichment process is the use of a highly overexpressed cell surface biomarker with high specificity and sensitivity for CTCs, such as the epithelial cell adhesion molecule (EpCAM). The Cellsearch System™ (Veridex), the only FDA-approved platform for CTC detection, utilizes anti-EpCAM antibody-coated magnetic nanoparticles to capture and enrich CTCs, followed by cytokeratin immunostaining. The AdnaTest (AdnaGen AG, Germany), another commercially available system for CTC detection, adopts similar immunomagnetic approach by using anti-EpCAM and Mucin 1 (MUC1) conjugated magnetic beads. More recently, "CTC chips" based on anti-EpCAM antibody-coated microfluidics chip were developed for CTC detection and enrichment (Nagrath et al, *Nature* 2007, 450:1235-9). However, the disadvantage of the above techniques is the low detection rate of pure CTCs, due to the non-specific binding of blood cells with anti-EpCAM antibody.

In order to maximize the detection and isolation of CTCs, it is necessary to reduce the nonspecific binding of other circulating blood cells. This can be achieved by surface modification with bioinert materials. For example, Kaladhar et al. observed a significant fewer circulating blood cells (e.g. platelets, leukocytes, and erythrocytes) binding onto the solid substrate modified with supported monolayer of various lipid compositions containing phosphatidyl-choline, cholesterol, and glycolipid (Kaladhar et al, *Langmuir* 2004, 20; 11115-22 and Kaladhar et al, *J Biomed Mater Res A* 2006, 79A:23-35).

Despite the advance in the detection and isolation CTCs technology, there is still a need for a more specific and effective method for detecting, purification and releasing CTCs and other biological substances for further cultivation and characterization.

BRIEF SUMMARY OF THE INVENTION

In one aspect, the present invention is directed to a surface coating to capture a circulating rare cell (CRC). This surface coating increases the capture efficiency of a CRC, such as CTC, circulating stem cells (e.g. tumor stem cell and bone marrow stem cells), fetal cells, bacteria, virus, epithelial cells, endothelial cells or the like and reduces the binding of non-specific cells or protein adsorption.

The surface coating comprises 1) a nonfouling composition at reduces the binding of nonspecific blood cells and adsorption of other blood components, such as protein; and 2) a bioactive composition that captures a CRC. The surface coating further comprises a linker composition that attaches to the nonfouling composition and the bioactive composition, as illustrated in FIG. 1A.

In another aspect, the present invention is directed to a surface coating to capture and release a biological substance. This surface coating increases the capture efficiency of a biological substance, such as CTC, circulating stem cells (e.g. tumor stem cell, liver stem cells and bone marrow stem cells), fetal cells, bacteria, virus, epithelial cells, endothelial cells or the like and enhances the removal or release of the non-specific cells or protein from the surface coating.

The surface coating comprises 1) a releasable composition for releasing or removing nonspecific blood cells and other blood components, such as protein, from the surface coating; and 2) a bioactive composition that captures a biological substance. The surface coating further comprises a linker composition that attaches to the releasable composition and the bioactive composition.

The present invention is also directed to a microfluidic device, with specific microstructure designs to create a disturbed flow of blood, body fluid or biological samples to increase the capture rate of the biological substance.

The present invention is also directed to a method of manufacturing the surface coating, comprising a) forming the nonfouling or the releasable composition; and b) attaching the the linker composition with the nonfouling/releasable composition from step a) and the bioactive composition, or c) attaching the nonfouling/releasable composition from step a) with the bioactive composition.

The present invention is also directed to methods to capture and release the biological substance from the surface coating. The biological substance on the surface coating can be purified by removing the non-specific cells or protein. The captured biological substance can be released by air bubbles, ultraviolet irradiation and the like.

The present invention is also directed to uses of a biotinylated anti-EpCAM antibody, EpAb4-1 antibody, to capture a CTC.

BRIEF DESCRIPTION OF THE DRAWINGS

Embodiments of the present invention may be described with reference to the accompanying drawings.

FIG. 15A to FIG. 15C are the photographs of the non-specific cells and the biological substance on the surface coating before and after the buffer rinse purification.

DETAILED DESCRIPTION OF THE INVENTION

The present invention is directed to a surface coating to effectively capture a circulating rare cell (CRC), such as CTC, circulating stem cells (e.g. tumor stem cell and bone marrow stem cells), fetal cells, bacteria, virus, epithelial cells, endothelial cells or the like.

In one embodiment, the surface coating for the capture of a CRC comprises 1) a nonfouling composition that prevents the binding of non-specific cells and adsorption of other blood components, such as protein; and 2) a bioactive composition that captures the circulating rare cells. The nonfouling composition and the bioactive composition are joined by discrete functional groups or moieties present in the nonfouling and bioactive compositions. Generally, a linkage between the two compositions is formed by an interaction comprising electrostatic interaction, hydrophilic-hydrophilic interaction, polar-polar interaction, complementary DNA binding, magnetic force, or combinations thereof.

In one group of embodiments, complementary DNA fragments are used for binding the nonfouling composition and the bioactive composition. The fragments are attached to each of the compositions and can be partially or completely complementary over their lengths. A suitable length of DNA will generally be at least 15, 20, 25, 35, 50, 100 or more bases in length. An example of the DNA used in the present invention is an DNA tweezer. (See, B Yurke et al. A DNA-fuelled molecular machine made of DNA. *Nature* 2000, 406:605-608.)

Figure 1A:
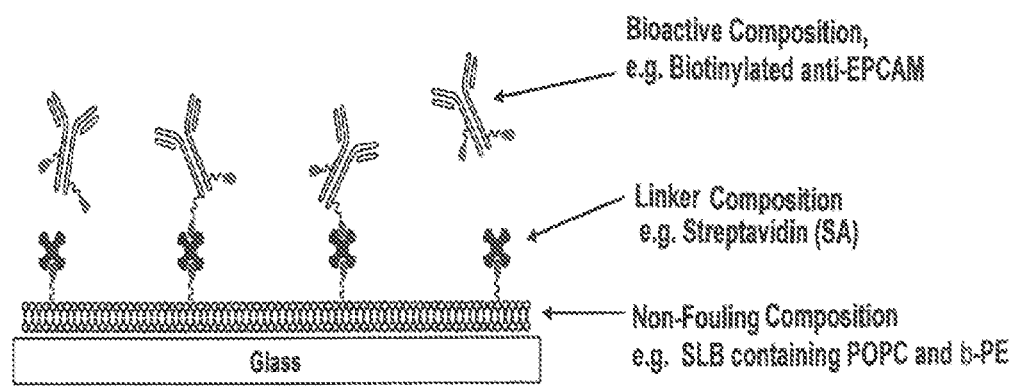
FIG. 1A illustrates schematically an embodiment of the surface coating comprising a nonfouling composition, a linker composition and a bioactive composition.

In another group of embodiments, the surface coating comprises 1) a nonfouling composition; 2) a bioactive composition; and 3) a linker composition, which joins the nonfouling composition to the bioactive composition. See FIG. 1A.

The present invention is also directed to a surface coating to effectively capture a biological substance, such as CTC, circulating stem cells (e.g. tumor stem cell, liver stem cells and bone marrow stem cells), fetal cells, bacteria, virus, epithelial cells, endothelial cells or the like, purify the biological substance on the surface of the surface coating by releasing or removing the non-specific cells and other serum components (e.g. protein) through a buffer rinse, and release the captured biological substance from the surface coating.

The surface coating for the capture and purification of a biological substance comprises 1) a releasable composition for releasing nonspecific blood cells and other blood components, such as protein, through a buffer rinse; and 2) a bioactive composition that captures a biological substance. The releasable composition and the bioactive composition are joined by discrete functional groups or moieties present in the releasable and bioactive compositions. Generally, a linkage between the two compositions is formed by an interaction comprising electrostatic interaction, hydrophilic-hydrophilic interaction, polar-polar interaction, complementary DNA binding, magnetic force, or combinations thereof.

In one embodiment, the surface coating further comprises a linker composition that attaches to the releasable composition and the bioactive composition.

As will be explained in more detail below, the surface coating can be incorporated into the following configurations: cell cultural dishes, microfluidic channels, microfluidic chips, filtration filter, capillaries, tubes, beads, nanoparticles, or the like, with an inner diameter ranging from about 50 to about 1000 um.

Nonfouling and Releasable Composition

The "nonfouling" composition (see FIG. 1A) reduces the binding of non-specific cells and adsorption of the serum protein.

The "releasable" composition comprises a nonfouling composition which also acts as a "lubricating" surface such that only low flow shear stress is required to remove or release the non-specific cells or blood components from the surface coating, while the biological substance remains intact.

Figure 2A:
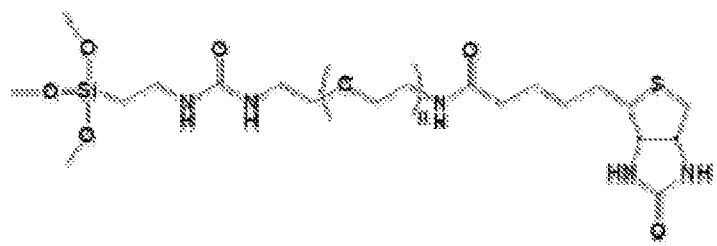
Figure 2B:
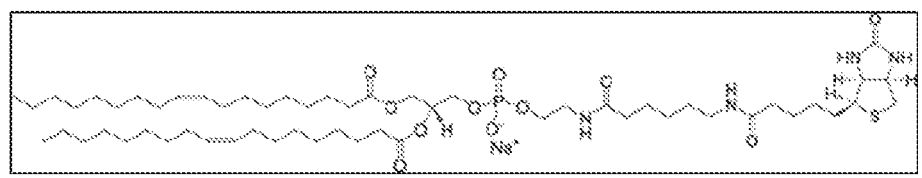
Figure 2C:
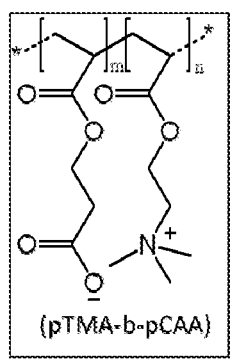
Figure 2D:
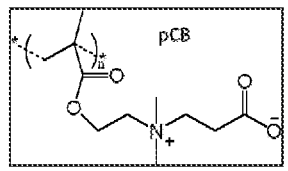
Figure 2E:
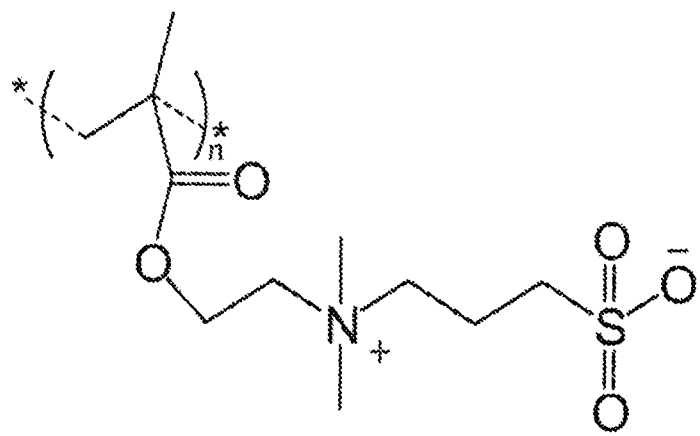
Figure 2F:
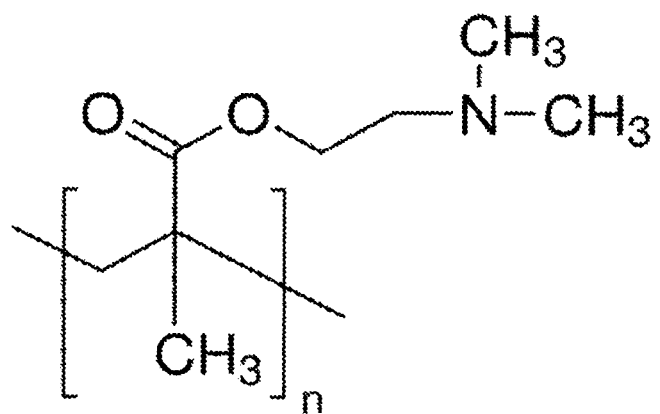
Figure 2F:
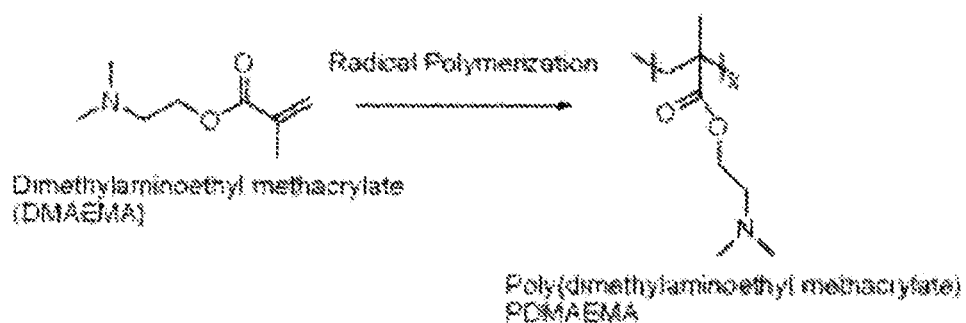

The nonfouling composition is selected from the group consisting of: a supported lipid layer such as liposomes, supported lipid bilayers (SLBs) or lipid multilayer, polypeptides, polyelectrolyte multilayers (PEMs), polyvinyl alcohol, polyethylene glycol (PEG) as illustrated in FIG. 2A, hydrogel polymers, extracellular matrix proteins, carbohydrate, polymer brushes, zwitterionic materials such as poly (carboxybetaine) (pCB)) as illustrated in FIG. 2D, poly (sulfobetaine) (pSB) as illustrated in FIG. 2E and pDMAEMA as illustrated in FIG. 2F, small organic compounds, and the combination of above materials forming a single or a multi-layer.

Figure 1B:
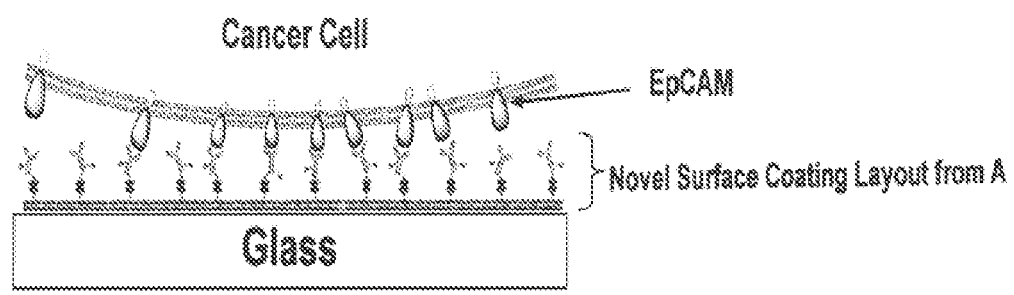
FIG. 1B illustrates schematically the binding of a circulating tumor cell with the surface coating from FIG. 1A FIG. 2A to FIG. 2F illustrate the chemical structures of examples of nonfouling materials.

For those embodiments in which the nonfouling composition comprises supported lipid bilayers (SLBs), the SLBs typically comprise lipids such as, for example, 1,2-diolcoyl-sn-glycero-3-phosphoethanolamine-N-(cap biotinyl) (sodium salt) (b-PE) as illustrated in FIG. 2B and 1-Palmitoyl-2-olcoyl-sn-glycero-3-phosphocholine (POPC). The protein resistant property of a SLB can be explained by the presence of neutral and zwitterionic phosphatidylcholine headgroups in a wide pH range, as well as an aqueous thin film formed between the hydrophilic lipid head groups and the bulk solution (see, Johnson et al. *Biophys J* 1991, 59:289-94).

In another group of embodiments, the nonfouling composition comprises PEG, preferably PEG with a molecular weight from about 100 to about 100,000 and exhibits a nonfouling property.

In yet another group of embodiments, the nonfouling composition comprises polyelectrolyte multilayers (PEMs) or a polymer brush. Examples of suitable PEMs useful in the present invention include, but are not limited to, poly-L-lysine/poly-L-glutamic acid (PLL/PLGA), poly-L-lysine/poly-L-aspartic acid or similar counter ionic polyelectrolytes. The polymer brush comprises ([2-(acryloyloxy)ethyl] trimethyl ammonium chloride, TMA)/(2-carboxy ethyl acrylate, CAA) copolymer as illustrated in FIG. 2C. Generally, the nonfouling layer has a thickness from a few nanometers up to hundreds microns.

The nonfouling composition comprises functional groups capable of covalent, non-covalent, or a combination of covalent and non-covalent attachment, either directly to a functional group present in the bioactive composition, or directly to a functional group that is part of the linkage composition.

In some embodiments, the functional groups of the nonfouling composition (prior to covalent attachment) are selected from: hydroxy groups, amine groups, carboxylic acid or ester groups, thioester groups, aldehyde groups, epoxy or oxirane groups, hyrdrazine groups and thiol groups, which are selected to be reactive with functional groups present in either the linker or bioactive composition. In other embodiments, the functional groups of the nonfouling composition (prior to non-covalent attachment) which are first members of a binding pair, are selected from the group using specific binding recognition consisting of avidin, streptavidin, DNA, RNA, ligand, receptor, antigen, antibody and positive-negative charges, each of which is selected to bind to a second member of the binding pair which is present in either the linker or bioactive composition.

The Linker Composition

The linker composition joins the nonfouling/releasable composition and the bioactive composition and comprises functional groups capable of covalent, non-covalent, or a combination of covalent and non-covalent attachment directly to a functional group present in the nonfouling/releasable composition and to a functional group that is part of the bioactive composition.

In some embodiments, the linker composition comprises functional groups (prior to covalent attachment) selected from: hydroxy groups, amine groups, carboxylic acid or ester groups, thioester groups, aldehyde groups, epoxy or oxirane groups, hyrdrazine groups and thiol groups, which are selected to be reactive with functional groups present in either the nonfouling or bioactive composition.

In other embodiments, the linker composition comprises functional groups (prior to non-covalent attachment) which are first members of a binding pair, selected from the group using specific binding recognition consisting of biotin, avidin, streptavidin, DNA, RNA, ligand, receptor, antigen, antibody and positive-negative charges, each of which is selected to bind to a second member of the binding pair which is present on the nonfouling/releasable composition or the bioactive composition.

The functional groups on the linker composition can also be a cleavable functional group, selected from: a photosensitive functional group cleavable by ultraviolet irradiation, an electrosensitive functional group cleavable by electro pulse mechanism, a magnetic material cleavable by the absence of the magnetic force, a polyelectrolyte material cleavable by breaking the electrostatic interaction, a DNA cleavable by hybridization, and the like.

Bioactive Composition

The bioactive composition joins to either the linker composition or the nonfouling composition, and comprises a binding moiety selective for the detection of the biological substance or CRC.

The bioactive composition comprises functional groups capable of covalent, non-covalent, or a combination of covalent and non-covalent attachment directly to a functional group present in the nonfouling layer or to a functional group that is part of the linker composition.

In some embodiments, the functional groups of the bioactive composition (prior to covalent attachment) are selected from: hydroxy groups, amine groups, carboxylic acid or ester groups, thioester groups, aldehyde groups, epoxy or oxirane groups, hyrdrazine groups and thiol groups which are selected to be reactive with functional groups present in either the nonfouling or linker composition. In other embodiments, the functional groups of the bioactive composition (prior to non-covalent attachment) are selected from the group using specific binding recognition consisting of biotin, avidin, streptavidin, DNA, RNA, ligand, receptor, antigen-antibody and positive-negative charges, each of which is selected to bind to a second member of the binding pair which is present on the nonfouling/releasable composition or the linker composition.

The binding moiety of the bioactive composition has specific affinity with the biological substance through molecular recognition, chemical affinity, or geometrical shape recognition. Examples of the binding moiety for the detection of the biological substance include, but are not limited to: synthetic polymers, molecular imprinted polymers, extracellular matrix proteins, binding receptors, antibodies, DNA, RNA, antigens or any other surface markers which present high affinity to the biological substance. A preferred antibody is the anti-EpCAM membrane protein antibody (commercially available from many sources, including R&D Systems, MN, USA), which provides high specificity for CTCs because EpCAM is frequently overexpressed in the lung, colorectal, breast, prostate, head and neck, and hepatic malignancies, but is absent from haematologic cells. Another preferred antibody is Anti-HER2, which has high specificity for CTCs but absent in haematologic cells.

In one embodiment, the anti-EpCAM membrane protein antibody is EpAb4-1 antibody, comprising a heavy chain sequence with SEQ ID No:1 and a light chain sequence with SEQ ID NO: 2 shown in Table 1.

TABLE 1

Amino Acid Sequence $V_H$ and $V_L$ domains of EpAb4-1 antibody

| | FW1 | CDR1 | FW2 | CDR2 |
|---|---|---|---|---|
| SEQ ID NO: 1 ($V_H$) | QIQUIQSGPELKKPGETV KISCKAS | GYTFTNYG MN | WVKQAPGKGLK WMGW | INTYT GEP |
| SEQ ID NO: 2 ($V_L$) | DIVMTQAAFSNPVTLGTS ASJSC | RSSKSLLH SNGITYLY | WYLQKPGQSPQ LLIY | HMSNL AS |

| | FW3 | CDR3 | FW4 | Family |
|---|---|---|---|---|
| SEQ ID NO: 1 ($V_H$) | TYGDDFKGRFAFSLETSA STAYLQINNLKNEDTATY FCAR | FGRSVDF | WGQGTSVINSS | $V_H$9 |
| SEQ ID NO: 2 ($V_L$) | GVPDRFSSSGSGTDFTLRI SRVEAEDVGIYYC | AQNLENPR T | FGGGTKLEIK | $V_K$24/ 25 |

Complementary-determining regions 1-3 (CDR1-3), framework regions 1-4 (FW1-4) for both the $V_H$ and $V_L$ domains are shown. The V domain families were aligned by VBASE2 database (www.vbase2.org).

The bioactive composition can have a variety of thicknesses, selected so that it does not affect the function or the performance of the surface coating.

Figure 3:
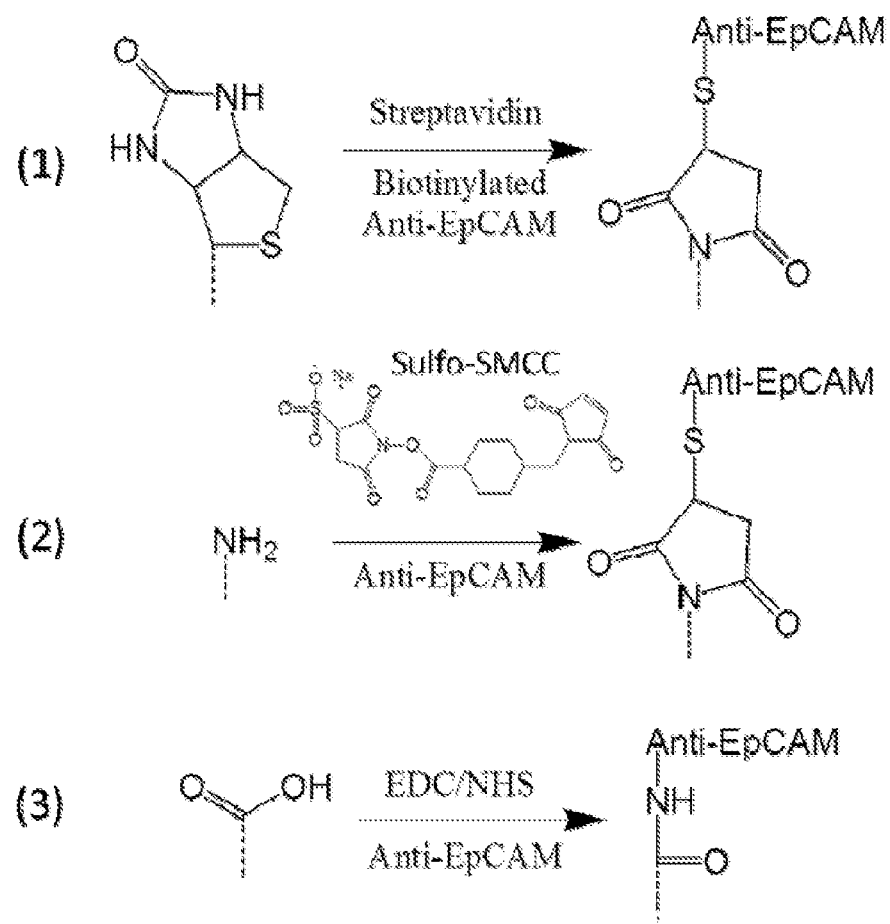
FIG. 3 illustrates the chemical reactions of conjugation between the functional groups on the nonfouling composition and the bioactive composition.

In one embodiment, the conjugation linkers or catalysts for the nonfouling composition and the bioactive compositions are biotinavidin or their derivatives. In another embodiment, the conjugation linkers or catalysts for the nonfouling composition and the bioactive composition are EDC/NHS. In yet another preferred embodiment, the conjugation linkers or catalysts for the nonfouling composition and the bioactive compositions are sulfo-SMCC. FIG. 3 schematically illustrates the chemical reactions of these embodiments.

Solid Substrate

Figure 4A:
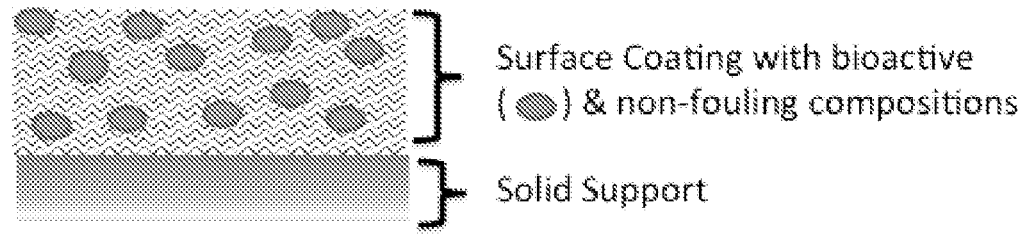
FIG. 4A illustrates schematically the attachment of the surface coating and solid substrate without a surface linker.
Figure 4B:
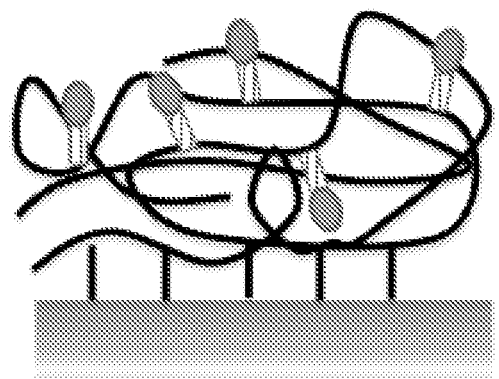
FIG. 4B and FIG. 4C illustrate schematically a linker composition with a cleavable functional group.
Figure 4C:
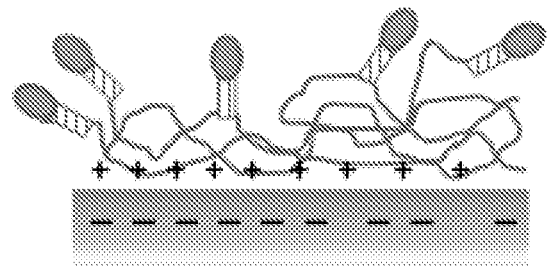

In some embodiments, the surface coating is attached to the solid substrate without a surface linker, as illustrated in FIG. 4A. The nonfouling/releasable composition is attached to the solid substrate via one of the following interactions: covalent bonding (for PEG nonfouling composition), hydrogen bonding, electrostatic interaction, hydrophilic-hydrophilic interaction (for SLB nonfouling/releasable composition), polar-polar interaction, complimentary DNA binding, magnetic force, or the like.

Figure 4D:
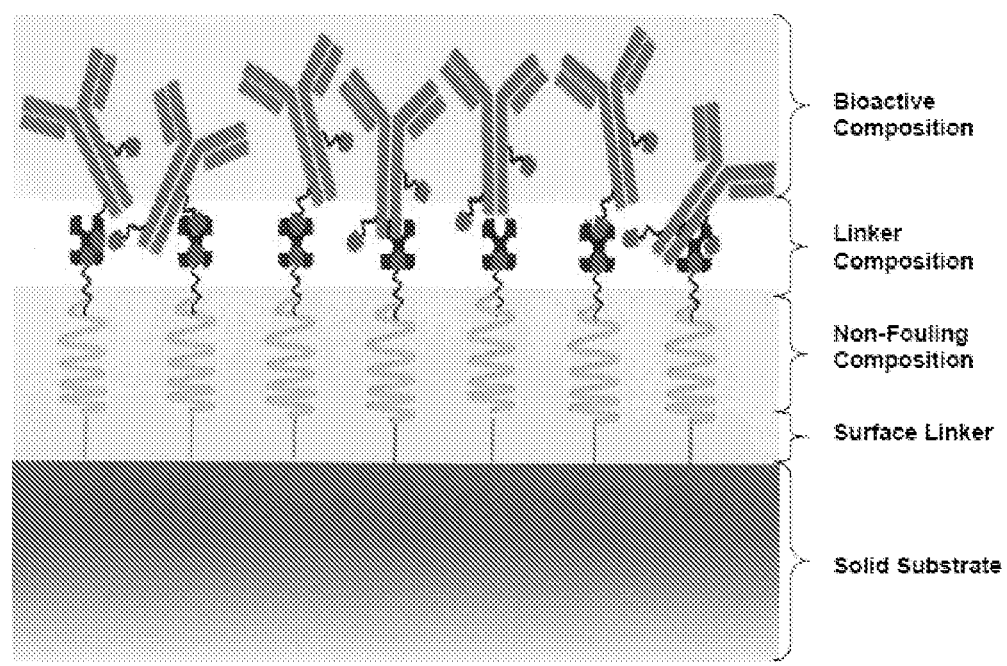
FIG. 4D illustrates schematically the attachment of the surface coating and the solid substrate using a surface linker.

In other embodiments, the surface coating is attached to the solid substrate with a surface linker, as illustrated in FIG. 4D. Examples of the solid substrate used in the present invention include, but are not limited to: metals, plastics, glass, silicon wafers, hydroxylated poly(methyl methacrylate) (PMMA), and a combination thereof. The shape of the solid substrate include, but are not limited to: planar, circular and irregular shapes with micro, or nano-structures such as nanoparticles, nanowires, and a combination thereof.

The surface linker composition comprises functional groups capable of covalent, non-covalent, or a combination of covalent and non-covalent attachment directly to a functional group present in the nonfouling/releasable composition and to a functional group that is part of the solid substrate. Examples of the surface linker for binding the surface coating to a glass substrate include, but are not limited to, silane, aminopropyltriethoxy aminopropyitrimethoxy silane, silane-PEG-NH$_2$, silane-PEG-N$_3$ (PEG molecular weight is about 1,000 to about 30,000 daltons) and silane-PEG biotin.

In one group of embodiments, the surface linker comprises a cleavable functional group selected from: a photosensitive functional group cleavable by ultraviolet irradiation, an electrosensitive functional group cleavable by electro-pulse mechanism, an iron or magnetic material in which the absence of the magnetic force will release the nonfouling composition, a polyelectrolyte material cleavable by breaking the electrostatic interaction, an DNA cleavable by hybridization, and the like.

In one embodiment, the nonfouling composition comprises silane-functionalized PEG and the solid substrate is preferably selected from the group consisting of silicon, glass, hydroxylated poly(methyl methacrylate) (PMMA) aluminum oxide, TiO$_2$ and the like. In another embodiment, the nonfouling composition comprises thiol-functionalized compounds and the solid substrate is preferably selected from the group consisting of Au, Ag, Pt, and the like.

The Method of Manufacturing the Surface Coating

Figure 5A:
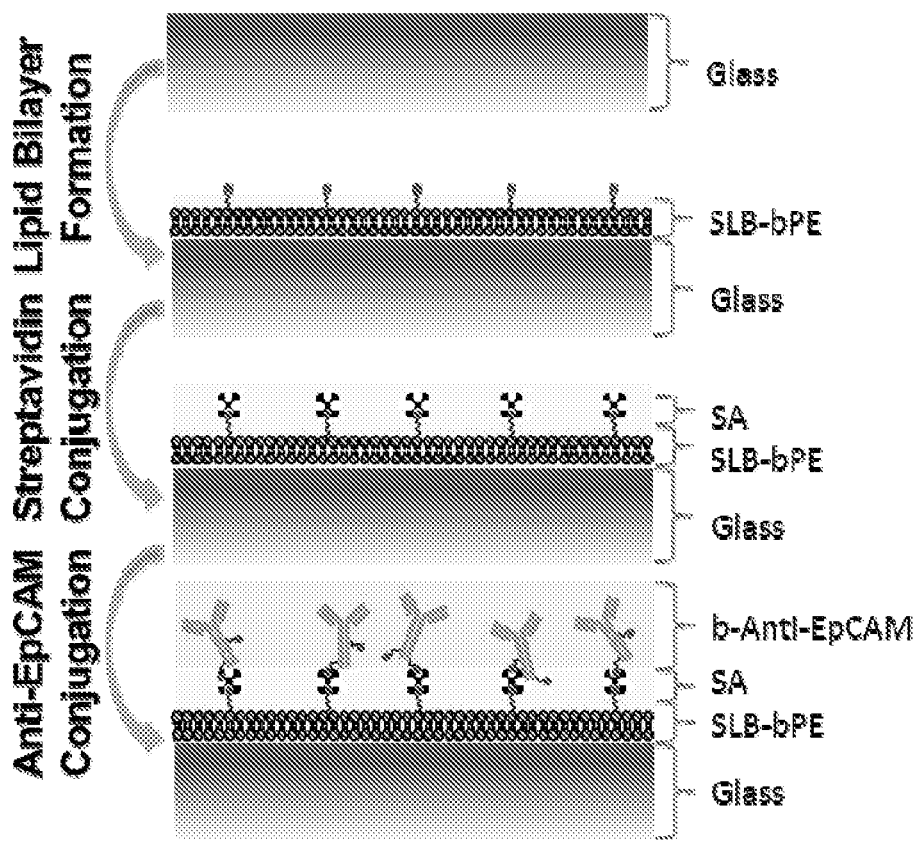
FIG. 5A and FIG. 5B illustrates schematically the formation of the surface coating on a solid substrate.
Figure 5B:
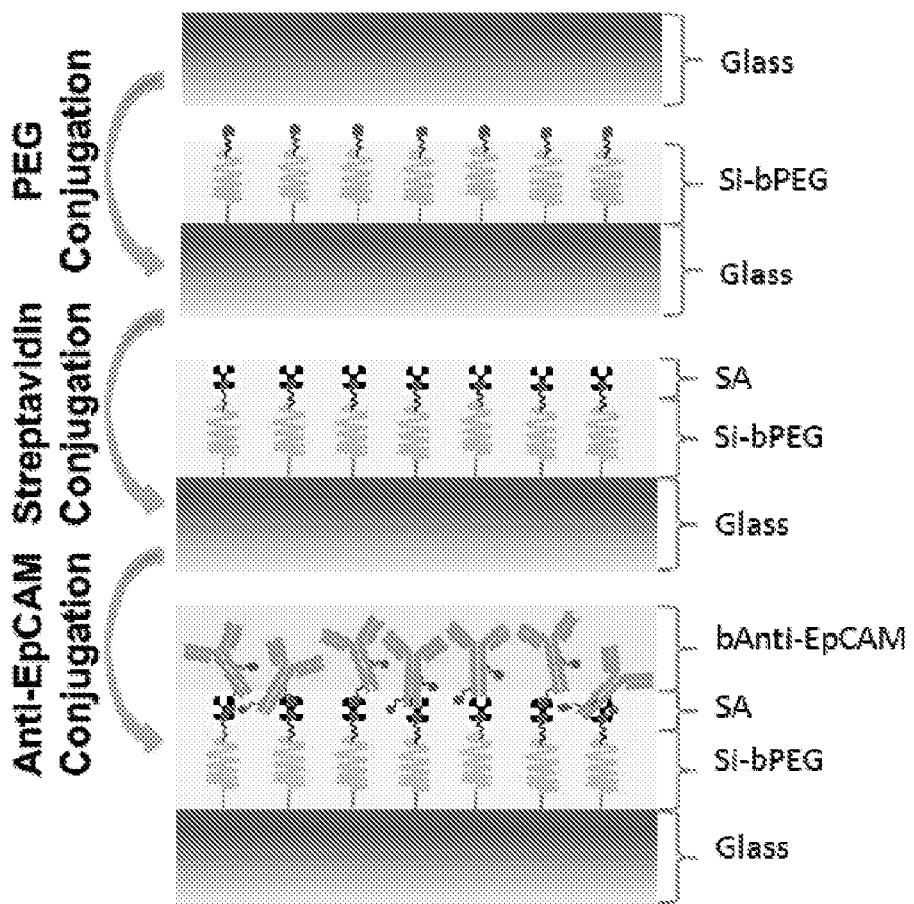

FIGS. 5A and 5B show the steps of forming the surface coating:
1. Formation of the nonfouling/releasable composition (e.g. SLB or PEG) with appropriate functional group (biotin);
2. Attaching the functional group (streptavidin) on the linker composition to the functional group (biotin) on the nonfouling/releasable composition;
3. Formation of the bioactive composition and attaching the functional group (biotin) on the bioactive composition to the functional group (streptavidin) on the linker composition.

The surface coating without a linker composition can be formed by:
1. Formation of the nonfouling/releasable composition with appropriate functional group (e.g. carboxyl group of N-glutaryl phosphatidylethanolamine or NGPE);
2. Formation and attaching the functional group (primary amine) on the bioactive composition to the functional group (carboxyl group of NGPE) on the nonfouling/releasable composition in step 1.

The steps in forming the surface coating as described above can be reversed, and the steps for forming the surface coating without a link composition as described above can be reversed.

Microfluidic Chip

Figure 6A:
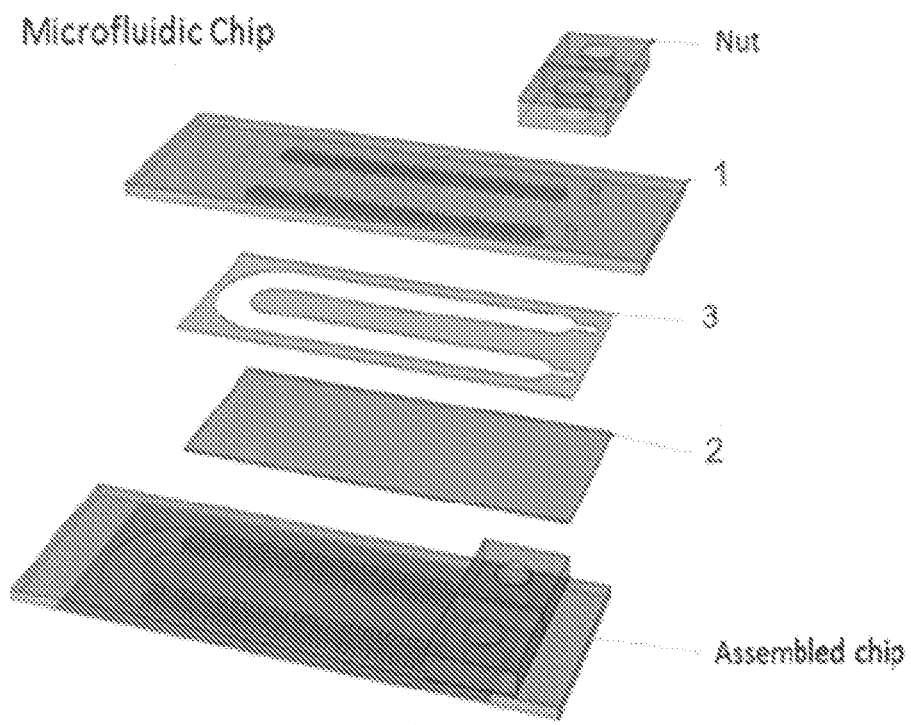
FIGS. 6A and 6B illustrate schematically the components of a microfluidic chip.

As illustrated in FIG. 6A, the microfluidic chip comprises a first solid substrate 1 (e.g. PMMA) and a second solid substrate 2 (e.g. glass), wherein the first and second solid substrates are adhered together using an adhesive means 3 or other means.

Figure 6B:
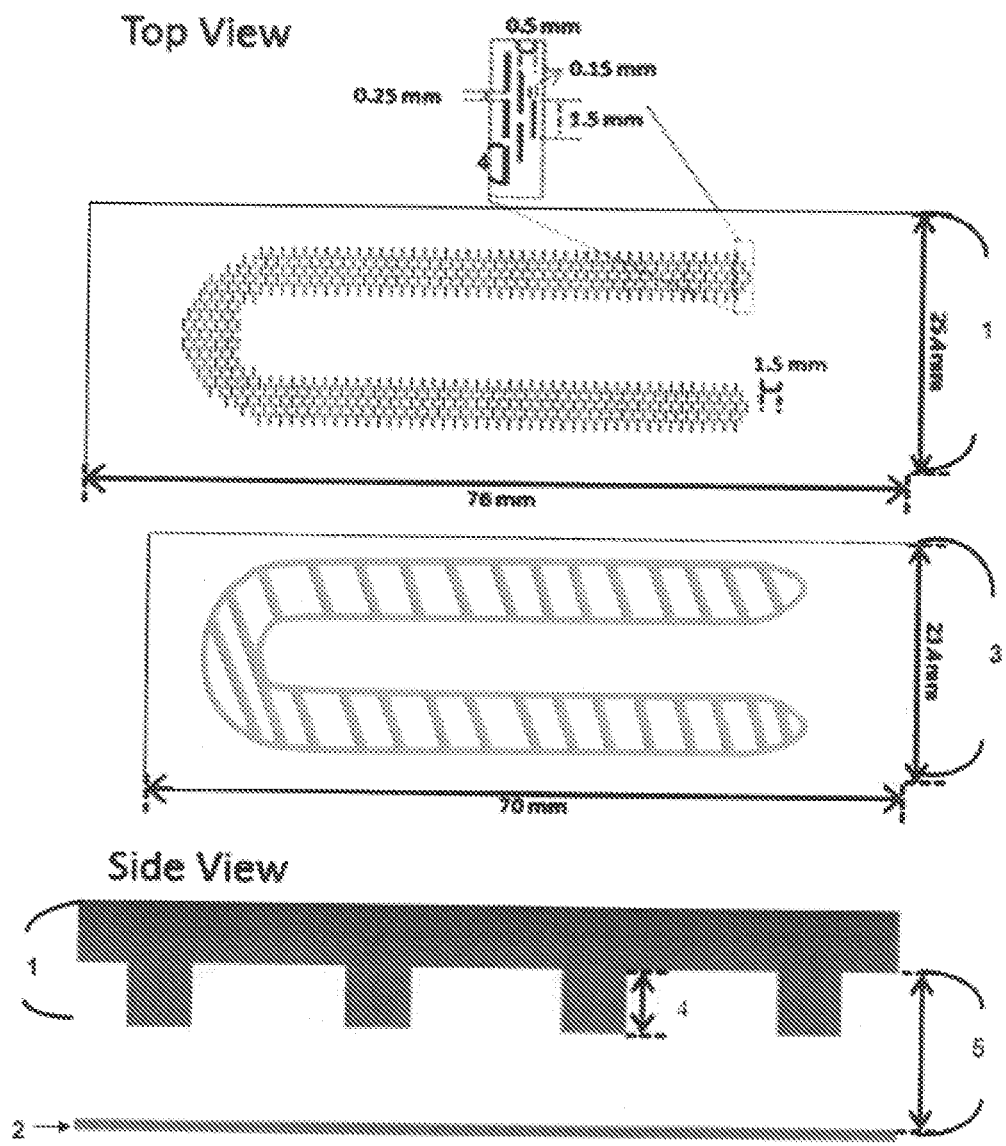

Referring to FIG. 6B, the surface of one or both solid substrates can be engraved with microstructures 4. In one group of embodiments, the microstructures 4 are arranged in a linear fashion. In another group of embodiments, the microstructures 4 are arranged in herringbone fashion. The shaded region on the adhesive 3 in FIG. 6B is carved out to accommodate the microstructures 4 on the surface of the solid substrate 1. A sealed channel 5 is created by adhering the first solid substrate 1 and the second solid substrate 2 together with an adhesive 3. The height of the channel 5 is determined by the thickness of the adhesive 3.

Once the microfluidic chip is formed, the surface coating can be attached to one or both solid substrates. In one group of embodiments, the surface coating is attached to the solid substrate with a surface linker. In another group of embodiments, the surface coating is attached to the solid substrate via one of the following interactions: covalent bonding (for PEG nonfouling composition), hydrogen bonding, electrostatic interaction, hydrophilic-hydrophilic interaction (for SLB nonfouling/releasable composition), polar-polar interaction, complimentary DNA binding, magnetic force, or the like.

Figure 6C:
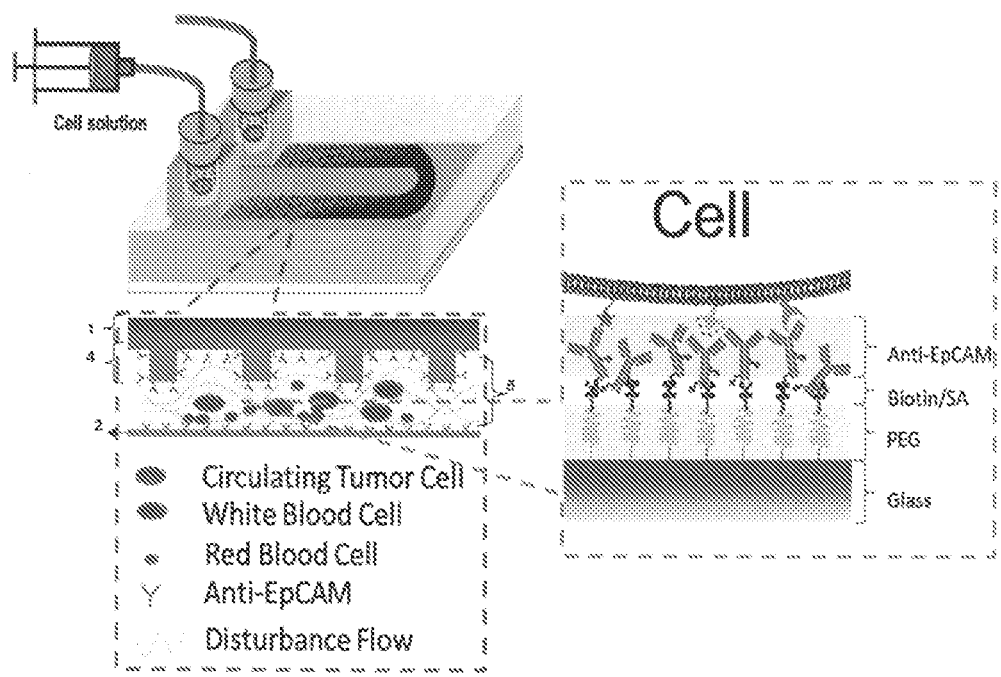
FIG. 6C illustrates schematically the microfluidic chip assembly to capture CTCs from a biological sample.

Referring to FIG. 6C, the microstructures 4 on the solid substrate 1 are perpendicular to the flow direction and create a chaotic or disturbed flow of the blood, body fluid or biologic sample as it passes through the sealed channel 5 of the microfluidic chip. The disturbed flow enhances the biological substance-surface coating contact.

Two factors govern the capture efficiency of the microfluidic chip:
(1) The linear speed of the blood, body fluid or biological sample, which determines the contact time of the biological substance and the surface coating. In a preferred embodiment, the linear speed is about 0.1 mm's to 1 mm's. In a more preferred embodiment, the linear speed is about 0.42 mm's or 0.5 ml/h for Design E in FIG. 7F.
(2) The flow disturbance of the blood, body fluid or biological sample, created by the microstructures 4 on the solid substrate(s). The flow disturbance increases contact between the biological substance and the surface coating.

Figure 7A:
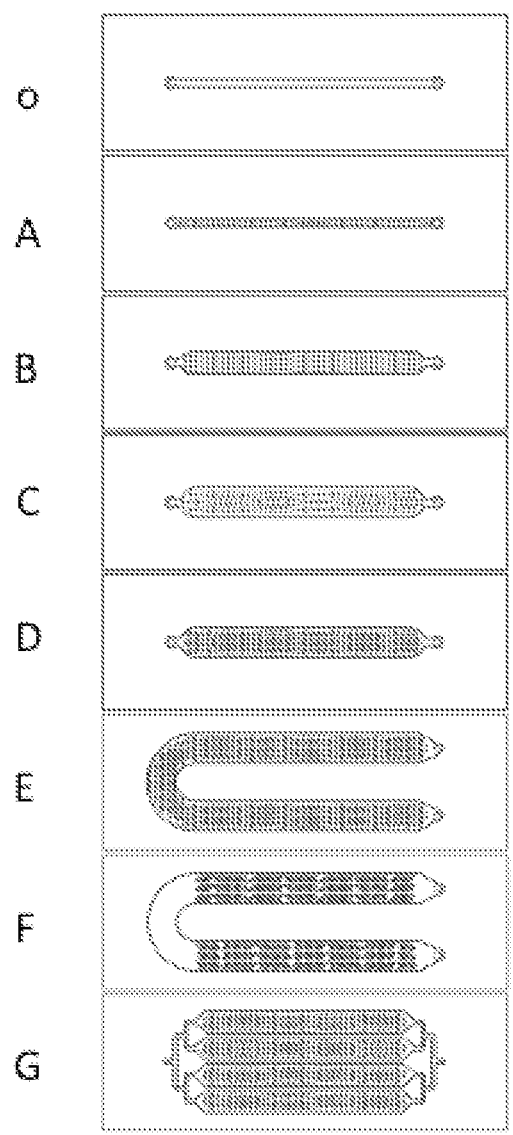
FIG. 7A to FIG. 7H illustrate schematically the designs of the microstructures on the solid substrate.
Figure 7B:
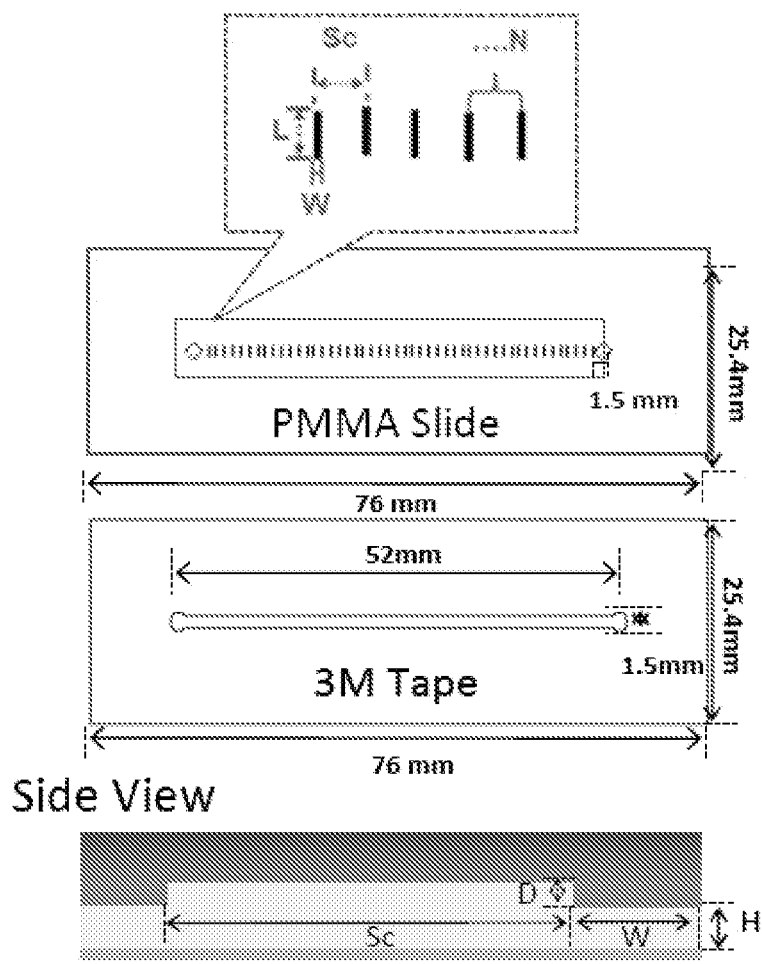
Figure 7C:
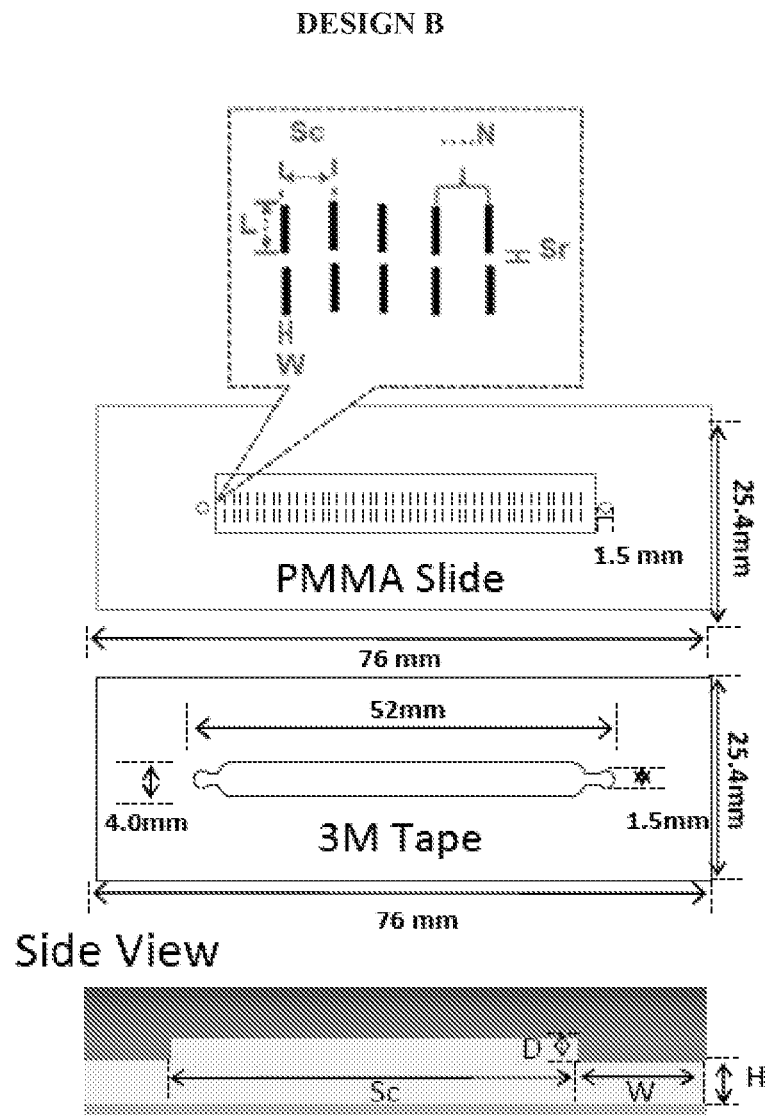
Figure 7D:
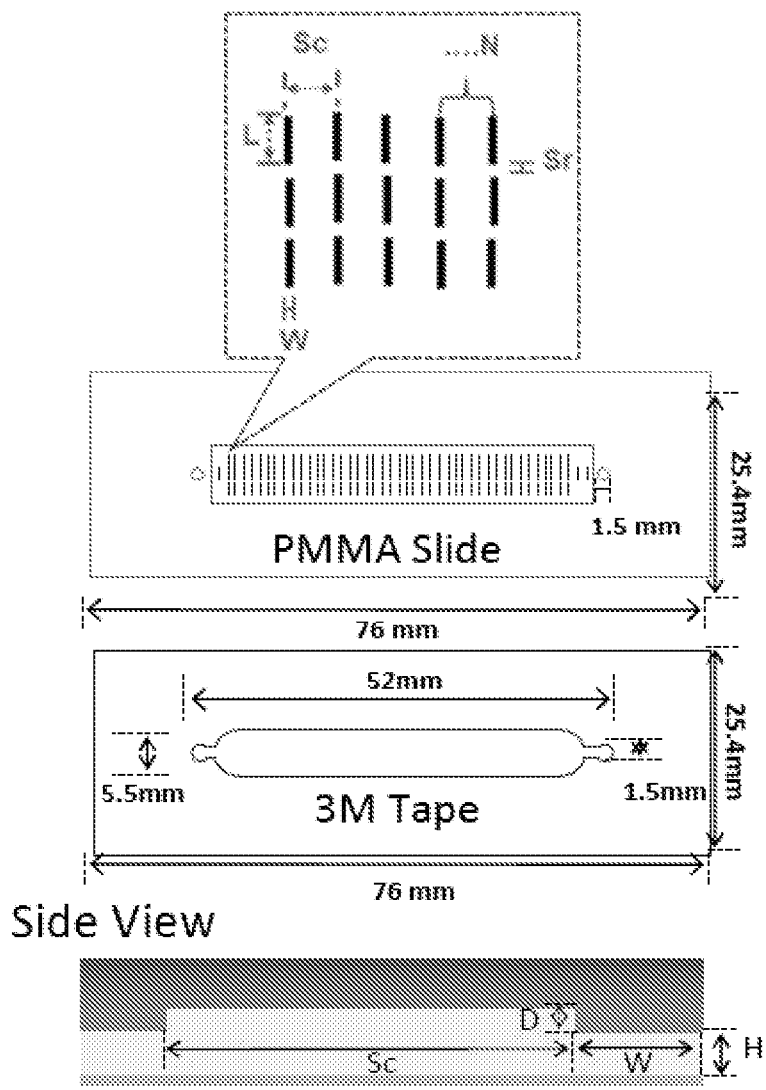
Figure 7E:
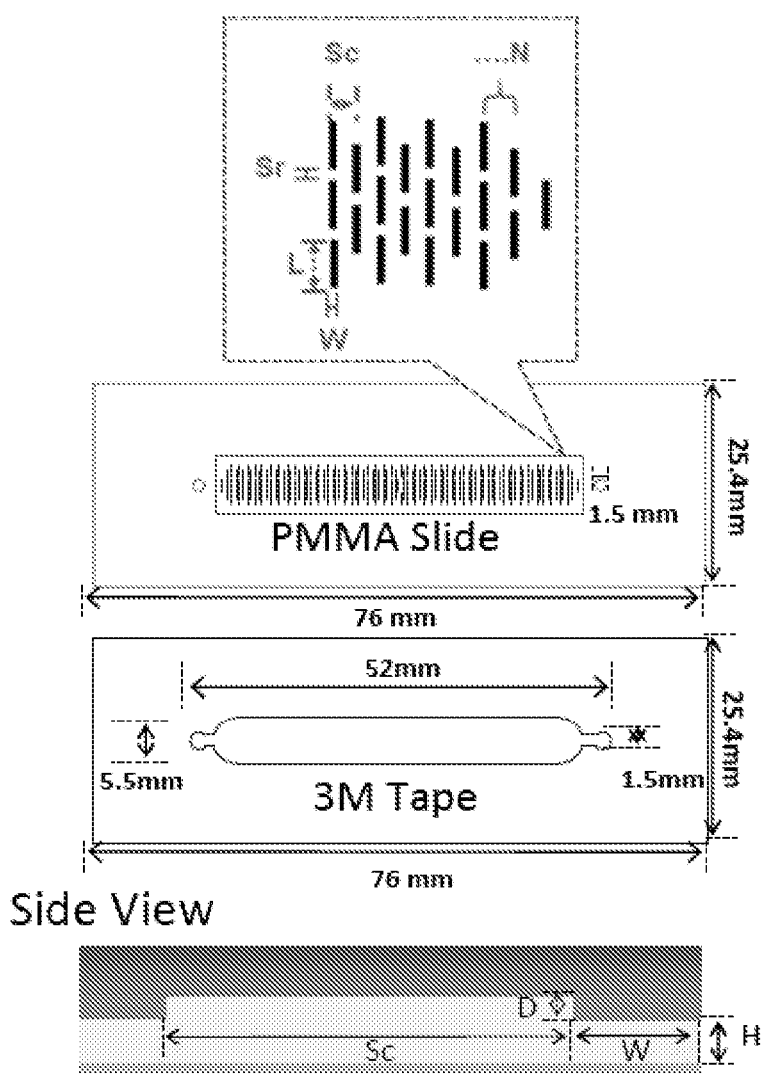
Figure 7F:
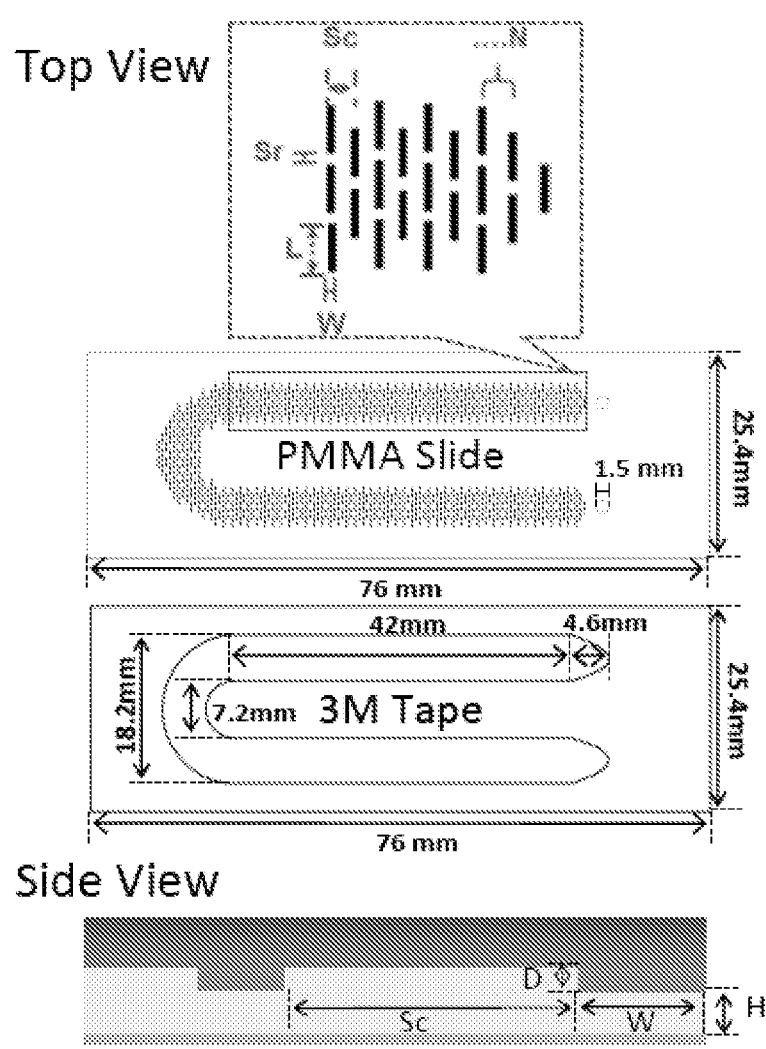
Figure 7G:
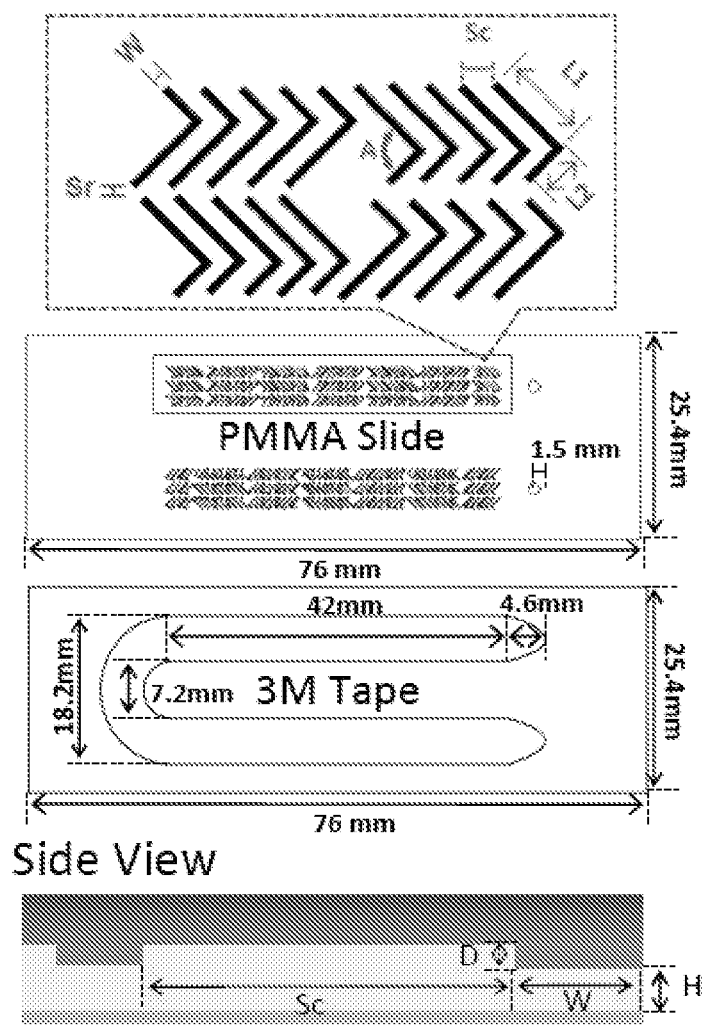

FIG. 7A shows various designs of the microstructures 4 on the solid substrate. The microstructures in Design F are arranged in a herringbone pattern whereas the microstructures in Designs A-E and H are arranged in a linear pattern. The dimensions of the microstructures 4 are as follows: the length is about 50 mm for O-D and G and about 120 mm for E-F, the height is about 30 µm, the width is about 1.5 mm for O and A, about 3.0 mm for B, and about 5.5 mm for C-G. The height of the sealed channel 5 varies with the thickness of the adhesive 3, preferably about 30-90 µm, more preferably about 60 µm.

Figure 7H:
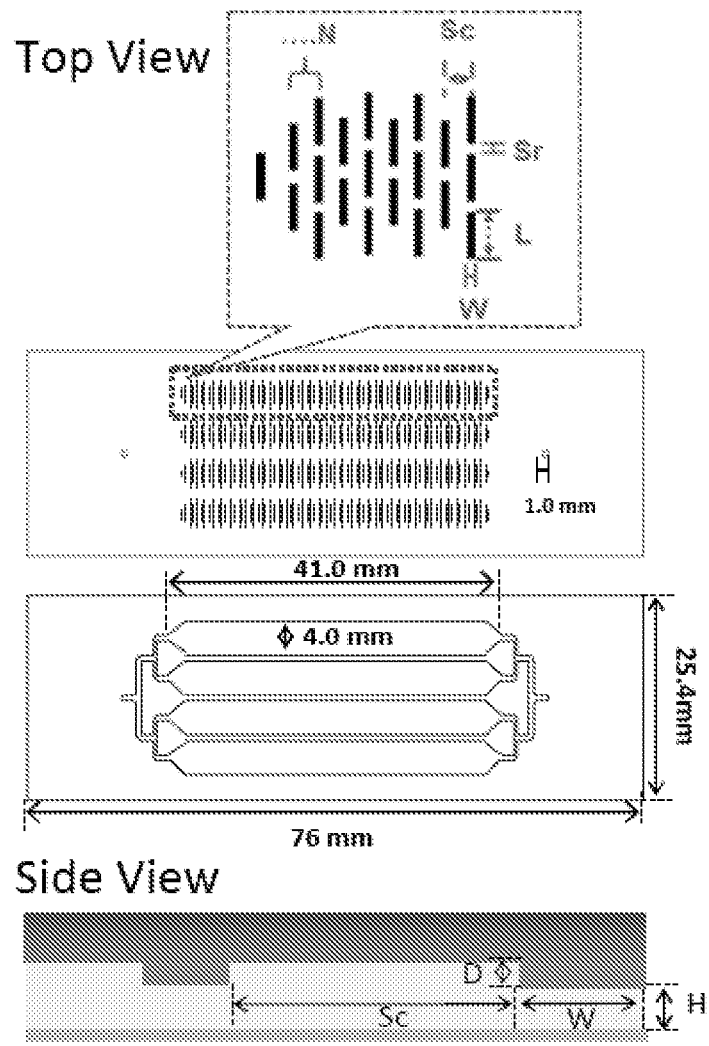

FIG. 7B-7H show the details of Designs A-G in FIG. 7A. Design G in FIG. 7H is the preferred pattern, with the following dimensions: the width of Microstructure (W) is about 150 µm, the length of microstructure (1) is about 1000 µm, the distance between two rows of microstructures (Sr) is about 250 µm, the distance between two adjacent microstructures (Sc) is about 350 µm, the height of the microstructure (D) is about 30 µm and the height of the sealed channel 5 (H) is about 60 µm.

Figure 7I:
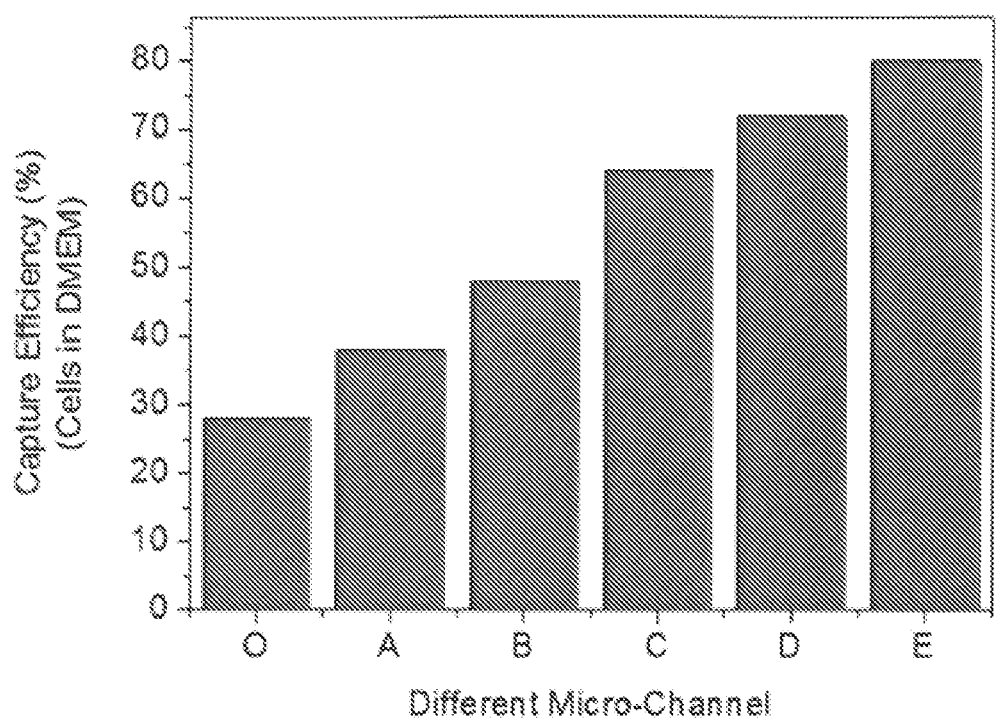
FIGS. 7I and 7J illustrate the capture efficiency of various microstructure designs in DMEM solution and blood respectively.
Figure 7J:
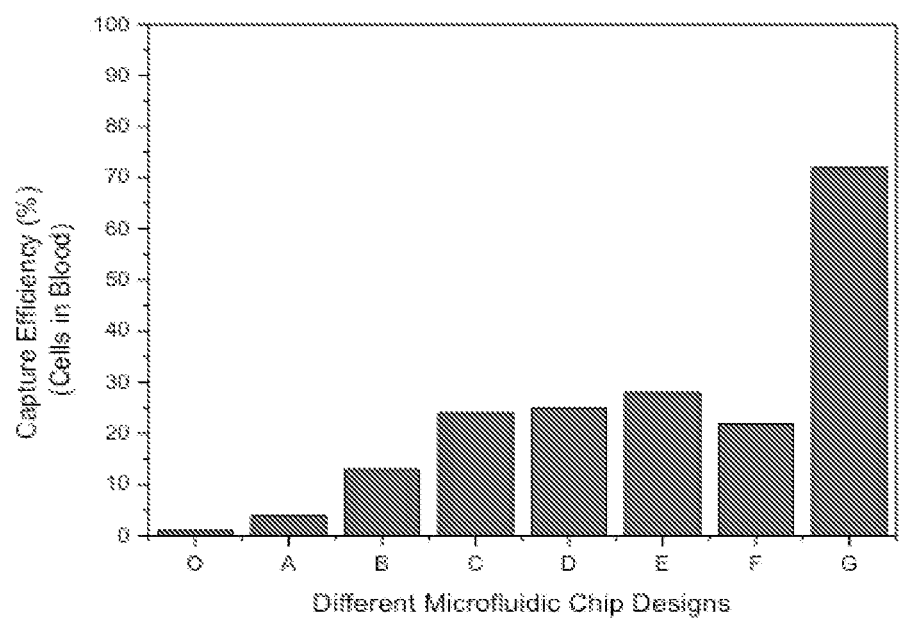

The biological substance capture efficiency of the various designs are shown in FIG. 7I and FIG. 7J. Capture rate is defined as (captured biological substance/original biological substance in the testing sample)×100%. Channel O has no microstructure and has the lowest biological substance capture rate, at 27% and 1% for DMEM sample and blood sample, respectively. Design E has a 80% capture rate for HCT116 cancer cells spiked in DMEM, and a 30% capture rate for HCT116 cancer cells spiked in blood sample. Design F has the best capture rate, on average over 70% of HCT116 cancer cells spiked in blood sample were captured (see FIG. 7J).

Flow Purification

The biological substance on the surface coating can be further purified by removing the non-specific cells and other blood components on the surface of the nonfouling/releasable composition. The nonfouling/releasable composition has low affinity for non-specific cells and other blood components. Therefore, rinsing the surface coating with a low flow buffer solution of about 0.8 dyne/cm$^2$ to about 50 dyne/cm$^2$ is sufficient to remove non-specific cells and other blood components on the nonfouling/releasable composition while the biological substance remains on the surface coating.

Figure 8:
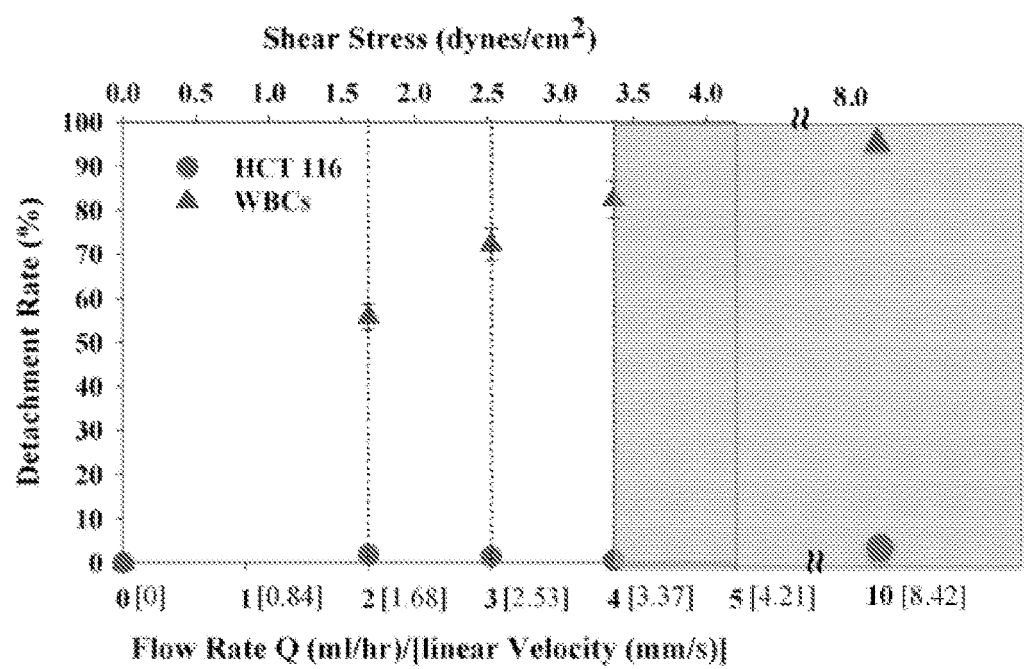
FIG. 8 illustrates the shear stresses of a buffer solution to release the non-specific cells and purify the captured biological substance.

In a preferred embodiment, the shear force of the buffer rinse is about 2.5 to about 10 dyne/cm$^2$. FIG. 8 shows that when the shear stress of the buffer flow is about 3.3 dyne/cm$^2$, 80% of the non-specific cells (i.e. white blood cells) were removed while none of the biological substance (i.e. HCT 116 cancer cells) were removed from the surface coating. When the shear stress of the buffer flow was increased to 8 dyne/cm$^2$, almost all of the non-specific cells were removed while none of the biological substance was removed from the surface coating.

Release of the Biological Substance

After removing the majority of the non-specific cells and blood components by flow purification, the biological substance can be released from the surface coating.

Figure 9:
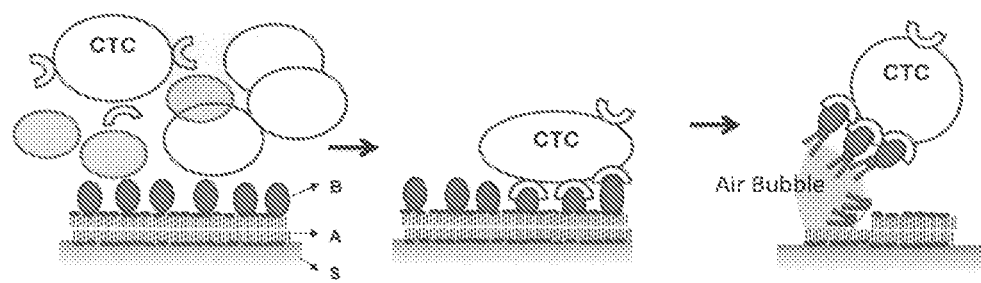
FIG. 9 illustrates schematically the release of biological substance by the air bubble method.

If the nonfouling/releasable composition comprises a lipid or a mixture of lipid, the captured biological substance can be released by introducing an air bubble solution or oil phase. As shown in FIG. 9, the surface coating comprises a nonfouling composition A (lipid bilayer) and a bioactive composition B (antibody) and is bound to a solid substrate S. The biological substance, CTC, is bound to the bioactive composition B, whereas other cells were repelled by the nonfouling composition A. As the air bubble approaches the lipid bilayer, the hydrophobic tails of the lipid bilayer are turned upside down due to its high affinity with the air inside the air bubble, which is also hydrophobic. This breaks up the hydrophilic-hydrophilic interaction at the surface of the lipid bilayer and allows the air bubble to "lift off" the top layer of the lipid bilayer, together with the CTC bound on the bioactive composition.

Figure 10A:
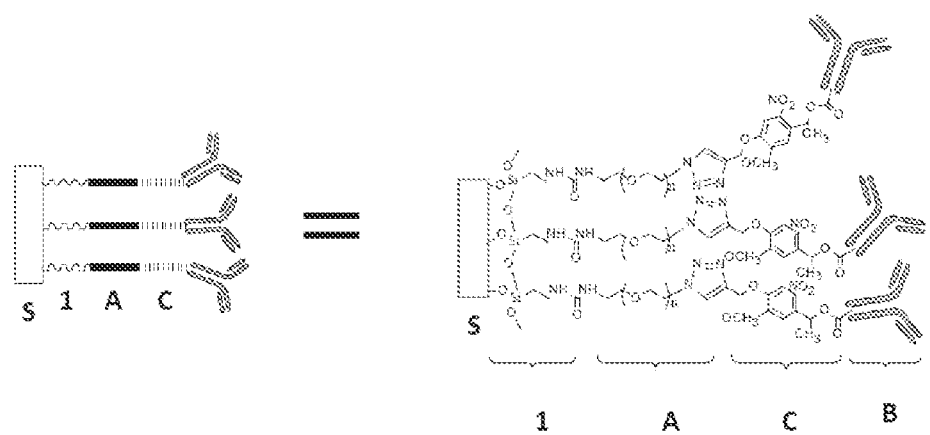
FIG. 10A illustrates schematically the surface coating with a cleavable linker composition on a solid substrate.
Figure 10B:
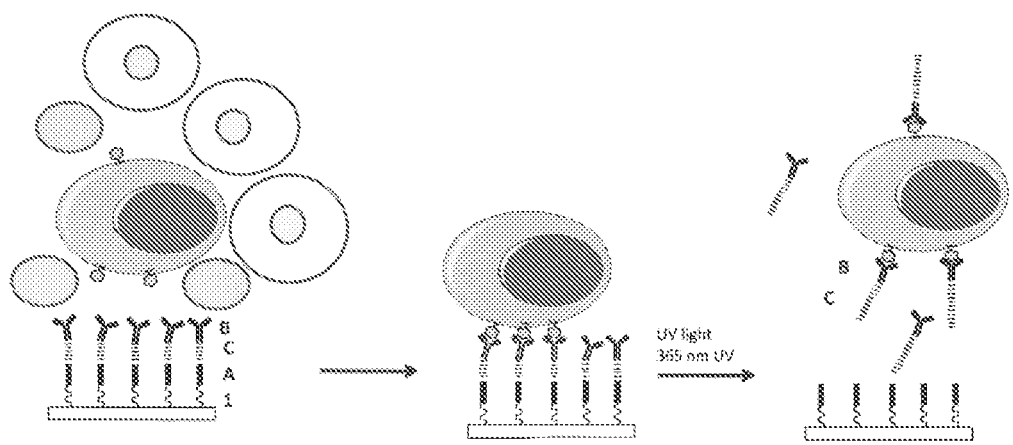
FIG. 10B illustrates schematically the release of the biologic substance from the surface coating in FIG. 10A.

If the nonfouling composition comprises a composition other than a lipid or a mixture of lipid, the captured biological substance can be released by breaking the cleavable functional group on the linker composition or on the surface linker. This release mechanism is illustrated in FIGS. 10A and 10B. FIG. 10A shows a surface coating on a solid substrate, wherein the surface coating comprises a bioactive composition B, a linker composition with a cleavable functional group C, and a nonfouling composition A. The surface coating is attached to a solid substrate S (e.g. glass) by a surface linker FIG. 10B shows the release of the biologic substance (e.g. CTC) from the surface coating in FIG. 10A. The biologic substance is bound to the bioactive composition B, whereas other cells were repelled by the nonfouling composition A. The surface coating is irradiated with 365 nm ultraviolet light, which breaks the cleavable functional group on the linker composition C and the biologic substance is released for subsequent analysis but maintaining the viability.

The biological substance can also be released by other mechanisms. In one group of embodiments, the linker composition or the surface linker comprises an electrosensitive cleavable functional group, and the biological substance is released by electro pulse mechanism. In another group of embodiments, the linker composition or the surface linker comprises a magnetic material as the cleavable functional group, and the absence of the magnetic field or force releases the biological substance. In yet another group of embodiments, the linker composition or the surface linker comprises a PEM as the cleavable functional group, and the biological substance is released by changing the electrostatic interaction between the layers. In yet another group of embodiments, the linker composition or the surface linker comprises an DNA piece as the cleavable functional group, and the biological substance is released by DNA hybridization.

EXAMPLES

The following examples further illustrate the present invention. These examples are intended merely to be illustrative of the present invention and are not to be construed as being limiting.

Example 1

Preparation of the Two-Layer Surface Coating

Preparation of the Nonfouling Composition:
Supported lipid bilayer (SLB) was prepared by the following steps:
(1) POPC and b-PE (commercially available from Avanti Polar Lipids, USA) were dissolved in chloroform and the final lipid concentration was 5 mg/mL. The POPCb-PE solution was vortex dried under a slow stream of nitrogen to form a thin, uniform POPCb-PE film. The POPCb-PE film was further dried in a vacuum chamber overnight to remove residual chloroform.
(2) The POPC/biotin-PE film in step (1) was dispersed in and mixed with a phosphate buffer containing 10 mM of phosphate buffered saline, 150 mM of sodium chloride aqueous solution, and 0.02% (w/v) of sodium azide (NaN$_3$, commercially available from Sigma-Aldrich, USA), with the pH adjusted to 7.2. The mixed solution was filtered through the 100-nm, followed by the 50-nm Nuclepore® track-etched polycarbonate membranes (Whatman Schleicher & Schuell, Germany) at least 10 times under 150 psi at room temp.
(3) The filtered solution in step (2) was passed through the LIPEX™ Extruder (Northern Lipids, Inc. Canada) to generate a homogenous population of unilamillar vesicles. The size of the POPC/biotin-PE vesicles was about 65±3 nm, determined by the dynamic laser light scattering detector (Zetasizer Nano ZS, Malvern Instruments, Germany).

Preparation of the Bioactive Composition
Biotinylated EpCAM Antibody was prepared by the following steps:
(1) The anti-EpCAM monoclonal antibody (OC98-1 or EpAb4-1) was generated by method described by Chen et al (Clin Vaccine Immunol 2007; 14:404-11).
(2) The antibody in step (1) was dissolved in a buffer solution containing 10 nM of PBS and 150 mM of NaCl, with a pH about 7.2. The concentration of the antibody buffer solution was about 0.65 mg/mL, determined by Nanodrop 1000 spectrophotometer (Thermo Scientific, USA).
(3) The antibody solution in step (2) was mixed with 10 mM of Sulfo NHS-LC-Biotin (with a molar ratio of 1 to 10) and dissolved in Milli-Q water (Milli-Q RO system, USA) at room temperature for 30 min. Excess biotin was removed by dialysis in phosphate buffered saline at 4° C. for 24 h, with a buffer change every 12 h.
(4) The ratio of biotin and antibody in the biotinylated anti-EpCAM antibody (OC98-1 or bEpAb4-1) was 1.5 to 1, determined by the HABA assay using a biotin quantitation kit (Pierce, USA).

Alternatively, commercially available biotinylated goat anti-human anti-EpCAM antibody from R and D Systems (Minneapolis, Minn.) could be used.

Preparation of Solid Substrates of the Present Invention
Glass substrate (such as microscope cove slips from Deckglaser, Germany) were cleaned with 10% DECON 90 (Devon Laboratories Limited, England), rinsed with Milli-Q water, dried under nitrogen gas, and exposed to oxygen plasma in a plasma cleaner (Harrick Plasma, Ithaca, N.Y., U.S.A.) at 100 mtorr for 10 min. Prior to each use, the glass substrate was rinsed with ethanol and dried under nitrogen gas.

Silicon oxide based solid substrates (e.g. silicon wafer or glass coverslips) were cleaned with piranha solution (70% sulfuric acid and 30% hydrogen peroxide (v/v)) at 120° C. for 40 min, subsequently washed with distilled water and rinsed with acetone. The solid substrates were dried under a stream of nitrogen and treated with a plasma cleaner.

For the vapor phase silanization reaction, clean silicon oxide substrates and a Petri-dish containing 150 uL of 3-(aminopropyl)-triethoxysilane (Sigma, USA) were placed in a desiccator (Wheaton dry-seal desiccator, 100 nm) under reduced pressure at ~0.3 Torr for 16 h. The substrates were cleaned by acetone and dried under nitrogen stream.

Construction of the SLB Surface Coating on a Solid Substrate
0.25 mg/ml of POPCb-PE vesicle solution described above was added to the cleaned solid substrate to form a SLB coated solid substrate. This was followed by an extensive rinse with a phosphate buffer containing 10 mM PBS and 150 mM NaCl (pH=7.2) to remove excess POPCb-PE vesicles. Biotin was the functional group in the SLB which binds with the functional group (streptavidin) in the linker composition.

0.1 mg/mL of streptavidin (SA) solution (commercially available from Pierce Biotechnology, Rockford, Ill., USA) was added to the SLB coated solid substrate and incubated for 1 hour, followed with a PBS buffer rinse to remove excess SA.

About 0.05 mg/mL of b-Anti-EpCAM solution was added to the SA-SLB coated solid substrate to form the surface coating of the present invention.

Construction of the PEG Surface Coating on a Solid Substrate

The biotinylated PEG silane solution (Si-bPEGs) was added to the clean glass substrate and incubated for 1 hour to form a Si-bPEG nonfouling composition on the glass substrate, followed by an ethanol rinse to remove excess Si-bPEGs. Silane was the surface linker and the biotin was the functional group that bind with the functional group (SA) in the linker composition.

0.1 mg/mL of SA solution was added to the Si-bPEGs coated solid substrate and incubated for 1 hour, followed by a PBS buffer rinse to remove excess SA.

0.05 mg/mL of b-Anti-EpCAM solution was added and bound with SA-Si-bPEGs surface coating, followed by PBS buffer rinse to remove excess b-Anti-EpCAM.

Construction of the PEM Surface Coating on a Solid Substrate

Physical deposition of PEM films was performed by batch and static conditions as follows: initially, all polypeptides were dissolved in 10 mM Tris-HCl buffer with 0.15 M NaCl, pH 7.4. Solid substrates were then immersed in PLL (MW 15000-30000; Sigma, St. Louis, Mo.) solution (1 mg/mL) for 10 min at room temperature, followed by rinsing with 10 mL of Tris-HCl buffer for 1 min. To couple PLGA, the PLL-coated slide was subsequently immersed in the PLGA solution (MW 3000-15000, Sigma, St. Louis, Mo., 1 mg/mL) for 10 min, followed by rinsing with 1 mL of Tris-HCl buffer for 1 min. Lastly, substrates were cleaned with fresh PBS to remove uncoupled polypeptides. The resulting c-(PLL/PLGA)i, where i was denoted as the number of polyelectrolyte pairs generated by repeating the above steps: i) 0.5 was referred to c-PLL only, i) 1 was referred to c-(PLL/PLGA)1, and the like.

QCM-D Characterization of the SLB Surface Coating

Figure 11:
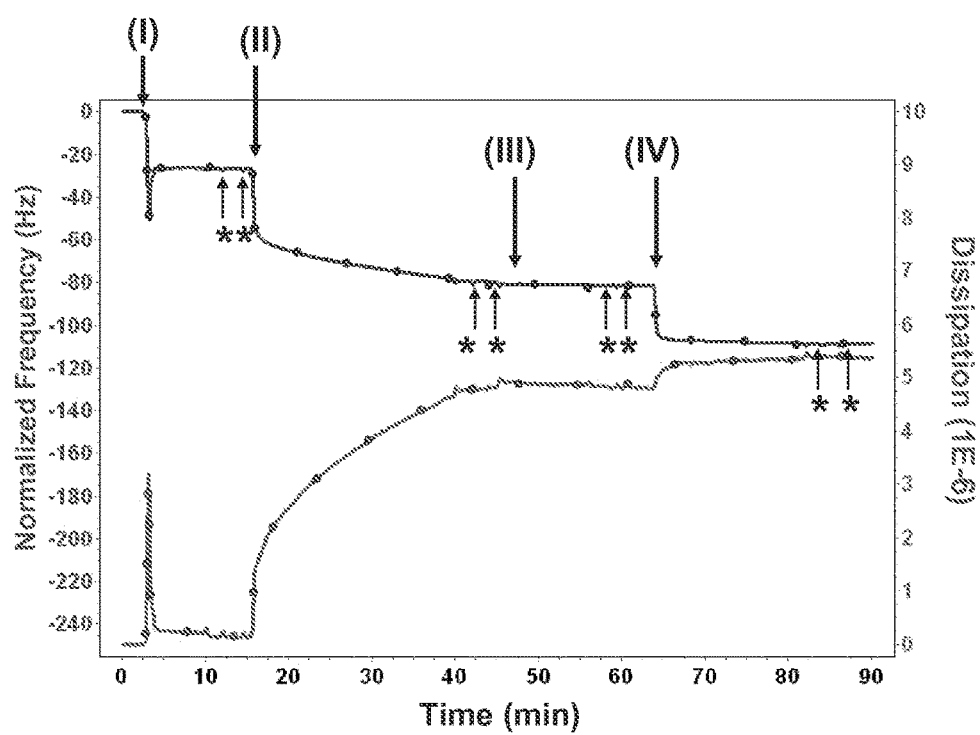
FIG. 11 illustrates QCM-D response of the surface coating construction.

The construction of the surface coating was monitored by quartz crystal microbalance with dissipation (QCM-D). The QCM-D response in FIG. 11 shows the construction of the surface coating on a $SiO_2$-pretreated quartz crystal. First, 0.25 mg/mL of POPCb-PE vesicle mixture (in phosphate buffer) was dispensed into the QCM chamber at point (I). The normalized frequency change F and dissipation shift D were 26.0±0.7 Hz and 0.19±0.03×10-6 respectively, which are the characteristics of a highly uniformed lipid bilayer. After two buffer washes (denoted as *), 0.1 mg/mL of SA solution was dispensed at point II, • SA binding was saturated at F=52.8±5.4 Hz and D=3.84±0.54×10-6. At point (III), 0.025 mg/mL of OC98-1 antibody solution was dispensed into the QCM chamber and there was no frequency or dissipation change. This shows there was no interaction between the OC98-1 antibody and the SA-lipid bilayer surface. In contrast, adding biotinylated antibody solution (bOC98-1 or bEpAb4-1) at point (IV) resulted in frequency and dissipation change, with equilibrated shifts of F=39.4±6.8 Hz and D=1.63±0.28×10-6. This demonstrates the binding of biotinylated antibody to SA-lipid bilayer surface.

Figure 12:
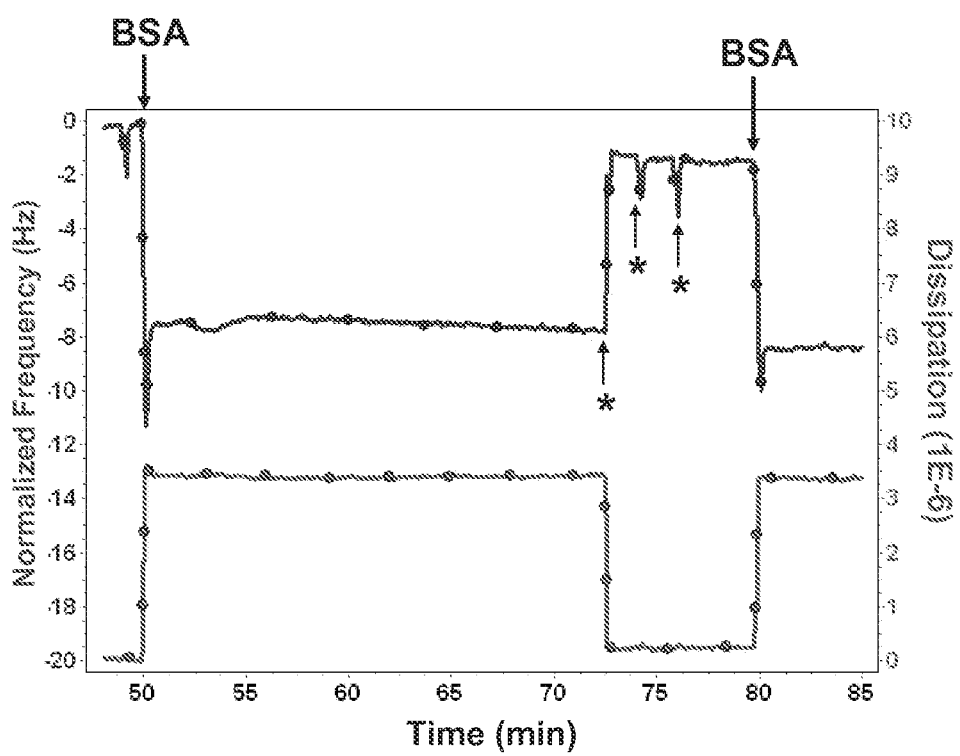
FIG. 12 illustrates the QCM-D response of the addition of bovine serum albumin to the surface coating.

The characteristics of the SLB nonfouling composition on the surface coating were examined using QCM-D (FIG. 12). Bovine serum albumin (BSA, commercially available from Sigma-Aldrich, USA) was added to the surface coating and there was a sudden change in frequency and dissipation, with equilibrated shifts of F=6.9 Hz and D=3.35×10-6. This indicates an immediate BSA adsorption. Three buffer rinses (*) caused an increase in frequency and a decrease in disspation, with saturated shifts of F=6.1 Hz and D=3.16×10-6. This indicates the adsorbed BSA can be easily removed from the surface coating and thus, a very weak interaction between BSA and SLB.

Example 2

Preparation of the Microfluidic Chip

The microfluidic chip can be prepared by the following steps:
1. A commercial $CO_2$ laser scriber (Helix 24, Epilog, USA) was used to engrave the microtrenches to form microstructures on the PMMA substrate.
2. The PMMA substrate, glass substrate and nuts were cleaned MeOH, detergent and water, followed by 10 min sonication. The nuts and the solid substrates were dried by nitrogen gas and baked for 10 min at 60° C.
3. The PMMA substrate s bonded with nuts by chloroform treatment.
4. PMMA substrate and the glass slide were joined together using an adhesive (e.g. 3M doubled sided tape from 3M, USA).

Example 3

CTCs Binding to the Anti-EpCAM Functionalized SLB Surface Coating

Eight blood samples were used to determine the CTC capture rate of the Anti-EpCAM functionalized SLB surface coating in a microfluidic chip in Example 2. Each blood sample contained 2 ml of blood from a stage IV colon cancer patient and the sample was introduced to the sealed channel of the microfluidic chip at 0.5 ml/hr, controlled by a syringe pump. Subsequently, the sealed channel in the microfluidic chip was rinsed with 0.5 ml of PBS buffer at the flow rate of 1 ml/hr, followed by in situ immunostaining.

The number of CTCs captured per ml of blood for these 8 samples were 26, 34, 36, 39, 47, 67 79, and 99. 25% of the blood samples had 79 or higher CTC count per ml of testing sample and the median CTC count was 43 per nil of testing sample. There was minimal binding of the non-specific cells and proteins after the buffer rinse.

As a comparison, the CTC count for the FDA approved Veridex CellSearch is as follows: 25% of the samples had 3 or more CTCs per 7.5 ml of testing sample and the median CTC counts was 0.

Figure 13:
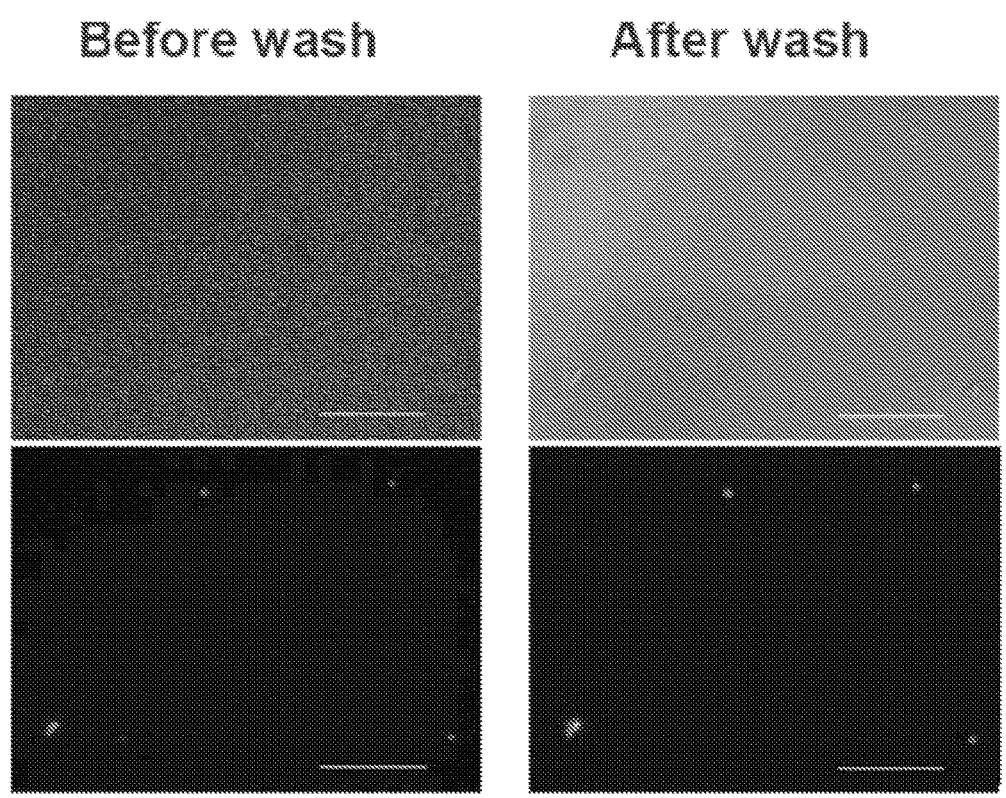
FIG. 13 are the photographs of the non-specific cells (top images) and the CTCs (bottom images) on the surface coating before and after the buffer rinse.

The anti-EpCAM functionalized SLB surface was incubated with 150 uL of HCT116 cancer cell spiked human blood (with HCT116 cancer cell density of approximately 10 to 100 per 100 μL of blood), followed by a buffer rinse to remove non-specific cells. FIG. 13 shows the surface coating before and after the buffer rinse. Prior to the buffer rinse, the surface coating was covered with non-specific cells (upper left) and four HCT116 cancer cells (lower left). After the buffer rinse, almost all of the non-specific cells were removed (upper right) but the four HCT116 cancer cell (lower right) remained on the surface coating.

The results show the surface coating of the present invention is effective in capturing CTCs and releasing the non-specific cells.

Example 4

Figure 14A:
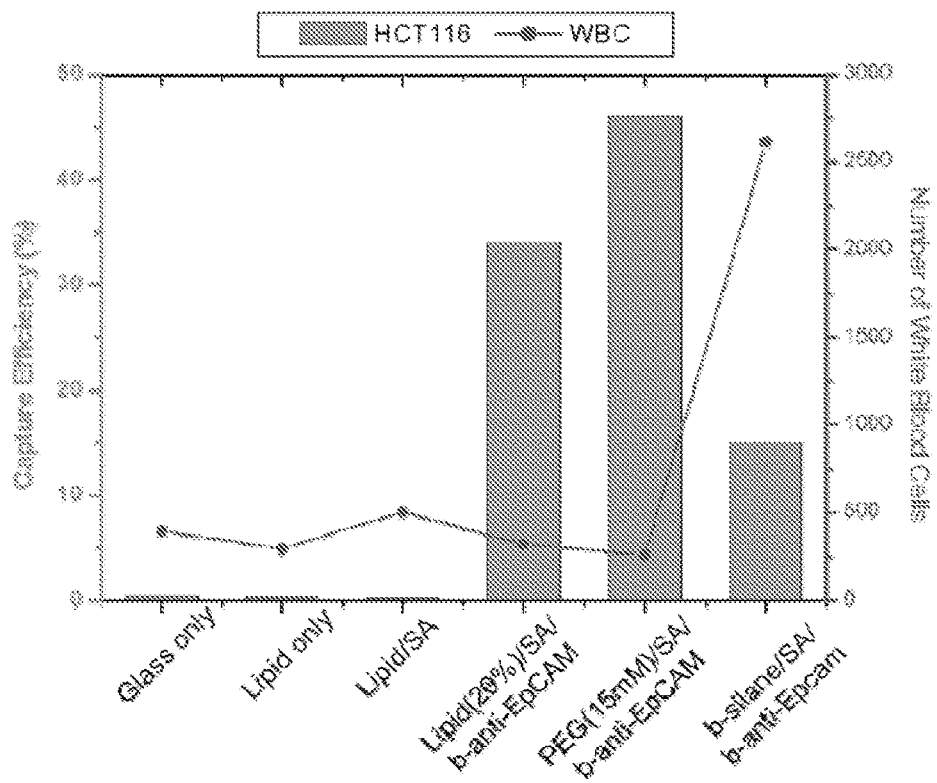
FIG. 14A illustrates the capture efficiency and non-specific blood cell binding of various surface coatings.
Figure 14:
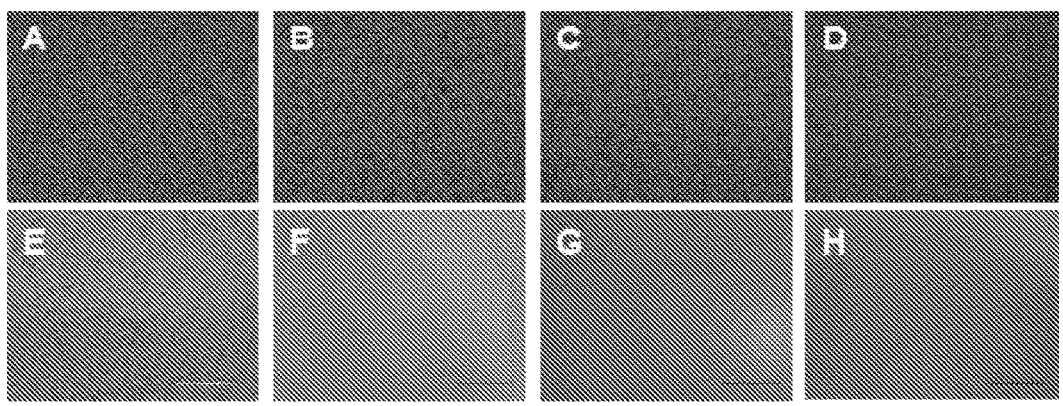
FIG. 14B are photo images which illustrate the non-specific blood cell binding of various surface coatings before and after the buffer rinse.

Comparison of Capture Efficiency and Nonfouling Property of Various Surface Conditions The capture rate of HCT116 cancer cells (biological substance) and the nonfouling property of six different surface conditions are illustrated in FIG. 14A.

The results show that the surface coatings of the present invention (lipid/SA/b-anti-EpCAM and PEG (15 mM)/SA/b-anti-EpCAM) are more effective in capturing the biological substance. There is less binding of the non-specific cells (white blood cells or WBC) on the surface coatings of the present invention compare to a surface coating without a nonfouling composition (glass only).

FIG. 14B shows the non-specific blood cell binding of the following surfaces: (A) Glass only; (B) biotinylated SLB (b-SLB), (C) Streptavidin conjugated-bSLB, and (D) OC98-1-conjugated bSLB. These surfaces were incubated with diluted human blood from healthy donor (1 uL of blood in 100 uL, PBS buffer) for 4 hours, followed by a PBS buffer rinse. Images (E) to (H) are the after rinse images which correspond to the surface coatings in (A) to (D). The results show that after a buffer rinse, there is less non-specific blood cell on the surface coatings with a releasable composition (i.e. SLB) compare to the surface coating without a releasable composition (i.e. glass only).

Example 5

Purification by Flow

The differentiated flow shear could selectively "flush" out the non-specific cells based on the affinity of these cells to the nonfouling composition, while the biological substance remains on the surface coating.

In this study, the surface coating comprised a SLB, a linker composition and fibronectin as the bioactive composition. FIG. 15A shows fibroblast 3T3 (green) and colon cancer cell line HCT116 (red) were incubated on the surface coating for 4 h. The surface coating was rinsed with a buffer solution, which has a shear stress of 3 dyne/cm$^2$.

The HCT 116 cells (red) were flushed away from the surface coating within 5 min of the buffer rinse, as shown in FIG. 15B. The fibroblast 3T3 cells (green) remained on the surface coating after 30 min of buffer rinse, as shown in FIG. 15C, due to its high affinity to fibronectin.

The result shows a shear stress about 3 dyne/cm$^2$ is sufficient to remove the non-specific cells from the releasable composition.

Figure 16:
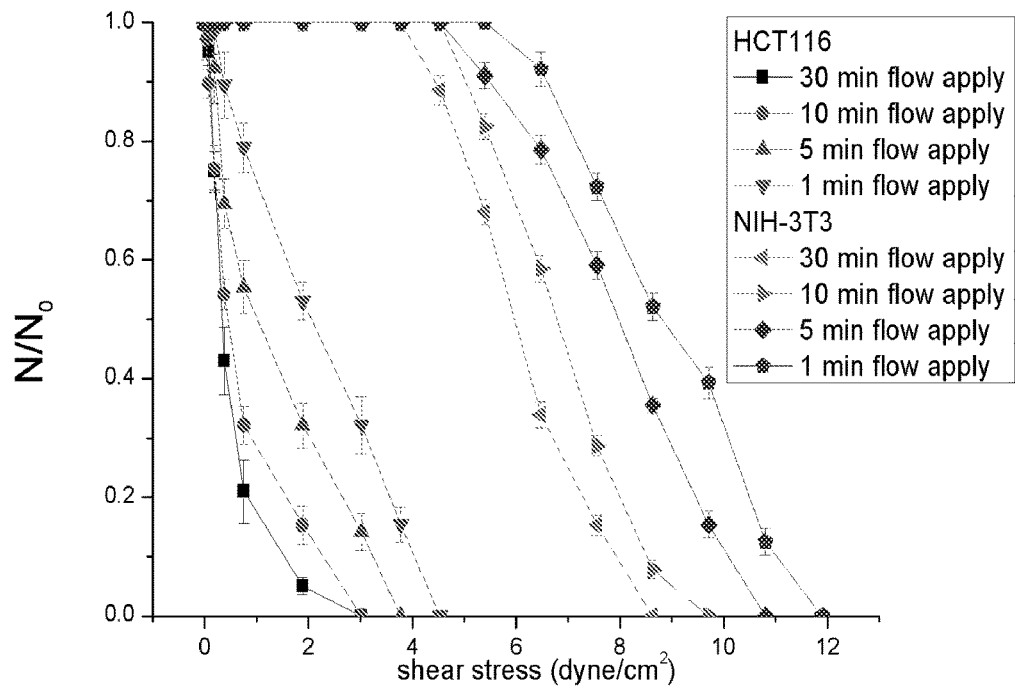
FIG. 16 illustrates the various shear stress and flushing time for the removal of HCT116 and NIH-3T3 cell populations from the surface coating.

FIG. 16 summarizes the respective shear stress and flushing time for the HCT116 and NIH-3T3 populations (non-specific cells). To remove HCT116 cells from the releasable composition of the surface coating, the shear stress is about 3 to about 4.5 dyne/cm$^2$. To remove NIH-3T3 cells from the releasable composition of the surface coating, the shear stress is about 8.5 to about 12 dyne/cm$^2$ (N/N0 is the percentage of the cells remains attached to the surface coating using various shear stresses, N is the final cell number and N0 is the initial cell number.)

Example 6

Release of CTCs from the Surface Coating

Figure 17:
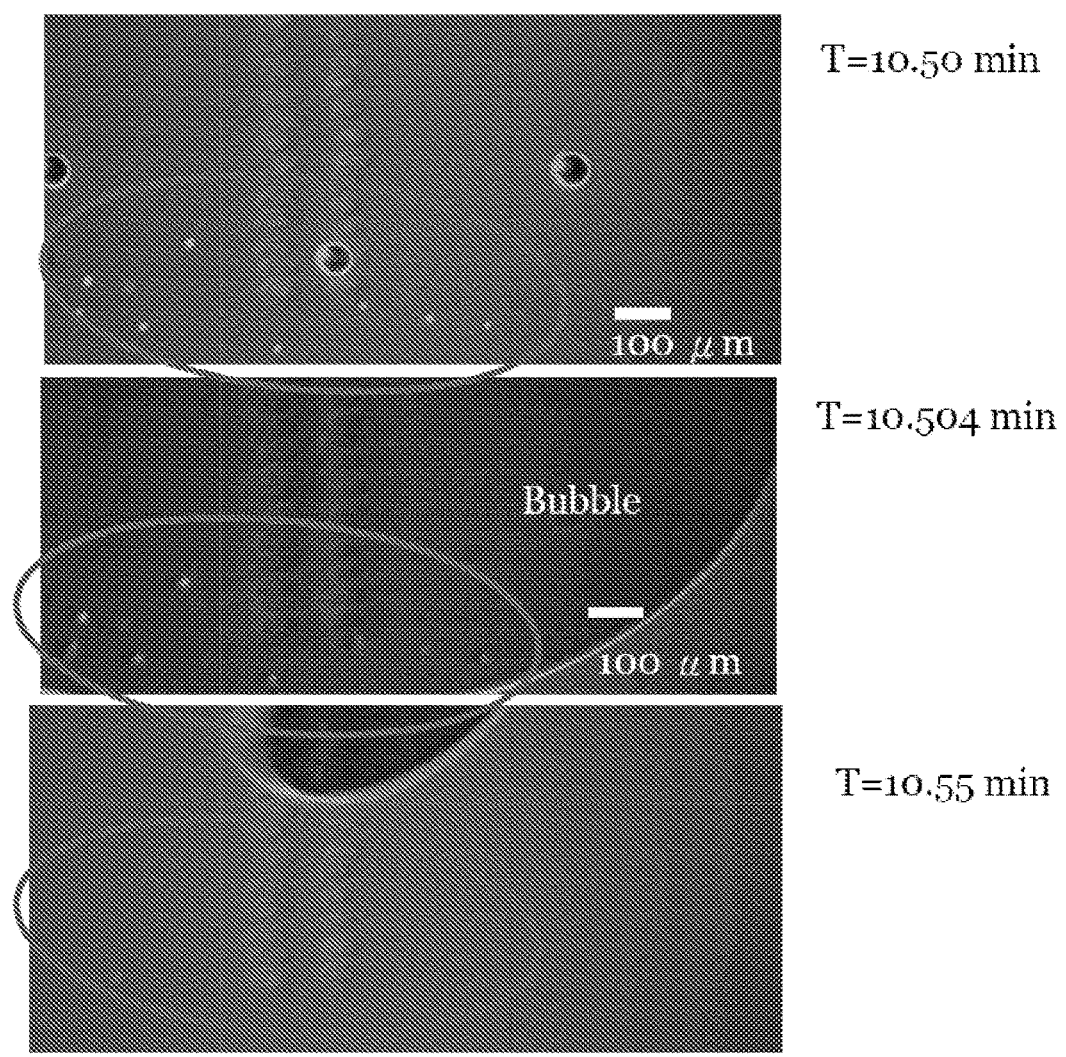
FIG. 17 are the photographs of the CTCs released by the air bubbles.

The captured HCT116 cancer cells on the surface coating in Example 3 were released by introducing air bubbles. FIG. 17 shows HCT116 cells in the red circle were removed from the surface coating within 3 seconds of introducing air bubbles.

Example 7

Culture of Released CTCs from the Surface Coating

The captured CTCs were incubated with 5 mM of EDTA at 37° C. for 5 to 10 min and released by flowing a culture medium into the sealed channel of the microfluidic chip. A total of 18 colo205 cells were released from this procedure. The released colo205 cells, together with a serum-containing culture medium and antibiotics (penicillin+streptomycin+gentamicin), were placed into a 48-well tissue cultured polystyrene plate for cultivation.

Figure 18:
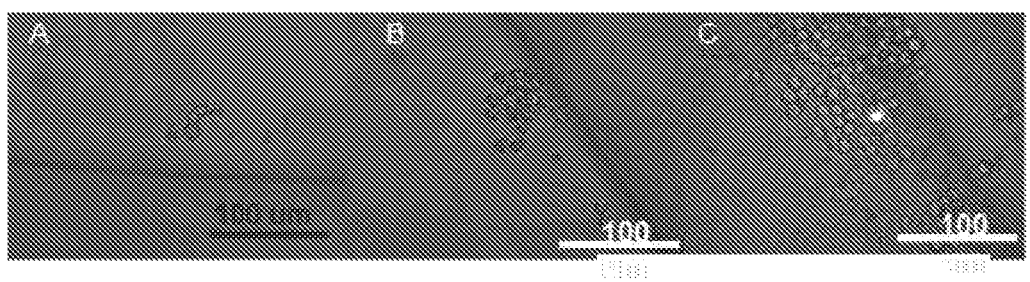
FIG. 18 illustrates the cell cultures of the released CTCs on day 1 day 10 and day 14.

FIGS. 18A-18C show a portion of 18 colo205 cells on day 1, on day 10 and day 14 respectively. This study demonstrates the released colo205 cells retained their viability for subsequent cell culture.

Example 8

Capture CTCs Through a CTC Filtration Device

Figure 19:
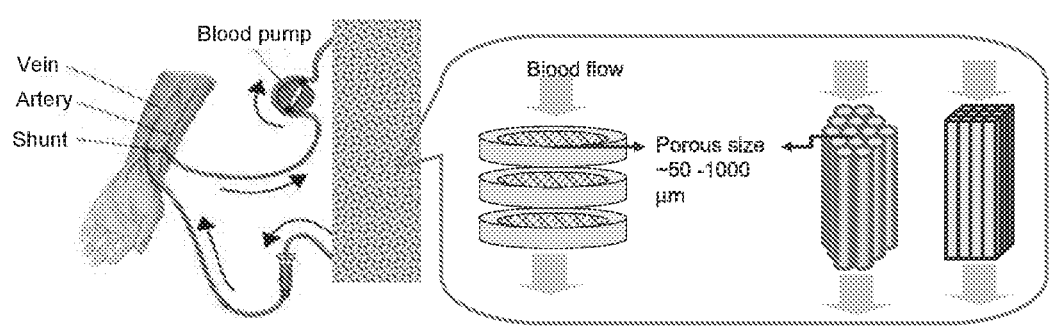
FIG. 19 illustrates schematically a CTC filtration device.

Any membranes, tubes, capillaries, beads, nanoparticles or channels can be coated with the surface coating of the present invention. FIG. 19 illustrates schematically a filtration device, wherein the filtration filter is coated with the surface coating of the present invention. The filter could accommodate high volume blood flow and capture a biological substance for a diagnostic or therapeutic purpose. To access the patient's blood or body fluid, a catheter can be inserted into the patient's vein or fistula and the patient's blood flows through the CTC filtration device, wherein the surface coating on the filters captures the CTCs. The filtered blood flows back to the patient.

Example 9

Capture CTCs Through a Biotinylated EpAb4-1 Antibody

The binding specificity of biotinylated OC9801 antibody, biotinylated EpAb4-1 antibody and biotinylated EpCam antibody (commercially available from R&D system, USA) were examined using the HCT116 (colorectal) CTCs and SAS (tongue) CTCs.

The CTCs were spiked in a buffer solution (about $10^5$ CTCs/ml). The CTC-spiked buffer solution was introduced to the surface coatings with the following bioactive composition: biotinylated OC9801 antibody, biotinylated EpAb4-1 antibody, biotinylated EpCam antibody and IgG antibody.

Figure 20:
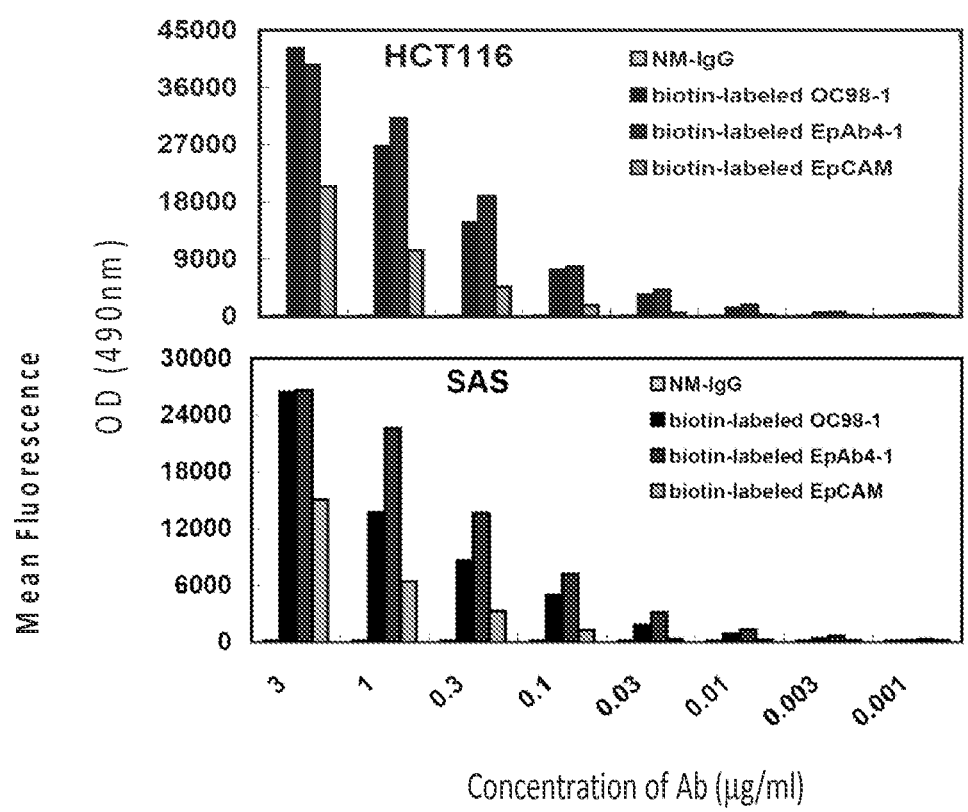
FIG. 20 illustrates the CTC binding specificity of biotinylated OC9801 antibody, biotinylated EpAb4-1 antibody, biotinylated EpCam antibody and IgG antibody.

The CTC binding specificity of the antibodies was determined by colorimetric method, by measuring the absorption optical density at 490 nm. FIG. 20 shows biotinylated EpAb 4-1 is effective in capturing HCT116 CTCs and SAS CTCs.

What is claimed is:

1. A method comprising:
   (a) contacting a biological sample comprising rare cells and non-specific cells to a non-fouling lipid layer of a microfluidic device, the microfluidic device comprising an antibody which selectively binds to rare cells, and wherein the non-fouling lipid layer is non-covalently associated with the antibody;
   (b) binding the rare cells to the antibody;
   (c) washing the non-fouling lipid layer with a liquid, wherein the non-specific cells in contact with the non-fouling lipid layer are released from the non-fouling lipid layer; and
   (d) flowing a liquid comprising bubbles through a channel of the microfluidic device of step (c), thereby releasing the rare cells from the microfluidic device.

2. The method of claim 1, wherein the released rare cells are viable.

3. The method of claim 2, further comprising collecting greater than 70% of the bound rare cells.

4. The method of claim 3, wherein the collected rare cells remain viable.

5. The method of claim 1, wherein the non-fouling lipid layer comprises a lipid monolayer.

6. The method of claim 1, wherein the non-fouling lipid layer comprises a lipid bilayer.

7. The method of claim 6, wherein air inside the bubbles has high affinity with hydrophobic tails of the lipid bilayer.

8. The method of claim 1, wherein the non-fouling lipid layer comprises liposomes.

9. The method of claim 1, wherein the non-fouling lipid layer is coupled to a solid substrate by a surface linker.

10. The method of claim 1, wherein the non-fouling lipid layer is from 2 nm to 300 μm thick.

11. The method of claim 1, wherein the rare cells are circulating tumor cells (CTCs).

12. The method of claim 1, wherein the antibody comprises a heavy chain and a light chain that binds EpCAM, wherein
   (a) the heavy chain comprises CDR1, CDR2, and CDR3 of SEQ ID NO: 1,
   (b) and the light chain comprises CDR1, CDR2, and CDR3 of SEQ ID NO: 2.

13. The method of claim 1, wherein the non-specific cells are selectively removed from the non-fouling lipid layer through application of the liquid at shear stress of from about 2.5 dyne/cm$^2$ to about 10 dyne/cm$^2$.

14. The method of claim 1, wherein the liquid comprising bubbles disrupts the non-fouling lipid layer and lifts off a top layer of the non-fouling lipid layer, together with the rare cells and bound antibody.

* * * * *

SEQUENCE LISTING

<160> NUMBER OF SEQ ID NOS: 2

<210> SEQ ID NO 1
<211> LENGTH: 116
<212> TYPE: PRT

```
<213> ORGANISM: Artificial Sequence
<220> FEATURE:
<223> OTHER INFORMATION: synthetic anti-epithelial cell adhesion
      molecule (EpCAM) membrane protein antibody EpAb4-1 heavy chain
      V-H9 domain
<220> FEATURE:
<221> NAME/KEY: PEPTIDE
<222> LOCATION: (1)..(25)
<223> OTHER INFORMATION: framework region 1 (FW1)
<220> FEATURE:
<221> NAME/KEY: PEPTIDE
<222> LOCATION: (26)..(35)
<223> OTHER INFORMATION: complementarity-determining region 1 (CDR1)
<220> FEATURE:
<221> NAME/KEY: PEPTIDE
<222> LOCATION: (36)..(50)
<223> OTHER INFORMATION: framework region 2 (FW2)
<220> FEATURE:
<221> NAME/KEY: PEPTIDE
<222> LOCATION: (51)..(58)
<223> OTHER INFORMATION: complementarity-determining region 2 (CDR2)
<220> FEATURE:
<221> NAME/KEY: PEPTIDE
<222> LOCATION: (59)..(98)
<223> OTHER INFORMATION: framework region 3 (FW3)
<220> FEATURE:
<221> NAME/KEY: PEPTIDE
<222> LOCATION: (99)..(105)
<223> OTHER INFORMATION: complementarity-determining region 3 (CDR3)
<220> FEATURE:
<221> NAME/KEY: PEPTIDE
<222> LOCATION: (106)..(116)
<223> OTHER INFORMATION: framework region 4 (FW4)

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Gly Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Phe Gly Arg Ser Val Asp Phe Trp Gly Gln Gly Thr Ser Val
            100                 105                 110

Thr Val Ser Ser
        115

<210> SEQ ID NO 2
<211> LENGTH: 112
<212> TYPE: PRT
<213> ORGANISM: Artificial Sequence
<220> FEATURE:
<223> OTHER INFORMATION: synthetic anti-epithelial cell adhesion
      molecule (EpCAM) membrane protein antibody EpAb4-1 light chain
      V-kappa24/25 domain
<220> FEATURE:
<221> NAME/KEY: PEPTIDE
<222> LOCATION: (1)..(23)
<223> OTHER INFORMATION: framework region 1 (FW1)
<220> FEATURE:
<221> NAME/KEY: PEPTIDE
<222> LOCATION: (24)..(39)
<223> OTHER INFORMATION: complementarity-determining region 1 (CDR1)
<220> FEATURE:
<221> NAME/KEY: PEPTIDE
```

```
<222> LOCATION: (40)..(54)
<223> OTHER INFORMATION: framework region 2 (FW2)
<220> FEATURE:
<221> NAME/KEY: PEPTIDE
<222> LOCATION: (55)..(61)
<223> OTHER INFORMATION: complementarity-determining region 2 (CDR2)
<220> FEATURE:
<221> NAME/KEY: PEPTIDE
<222> LOCATION: (62)..(93)
<223> OTHER INFORMATION: framework region 3 (FW3)
<220> FEATURE:
<221> NAME/KEY: PEPTIDE
<222> LOCATION: (94)..(102)
<223> OTHER INFORMATION: complementarity-determining region 3 (CDR3)
<220> FEATURE:
<221> NAME/KEY: PEPTIDE
<222> LOCATION: (103)..(112)
<223> OTHER INFORMATION: framework region 4 (FW4)

<400> SEQUENCE: 2

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr His Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Ile Tyr Tyr Cys Ala Gln Asn
                85                  90                  95

Leu Glu Asn Pro Arg Thr Phe Gly Gly Gly Thr Lys Leu Glu Ile Lys
            100                 105                 110
```